(12) United States Patent
Mehnert

(10) Patent No.: US 11,618,920 B2
(45) Date of Patent: *Apr. 4, 2023

(54) METHOD FOR ANALYZING NUCLEIC ACID SEQUENCE

(71) Applicant: SYSMEX CORPORATION, Kobe (JP)

(72) Inventor: Daniel Mehnert, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 75 days.

This patent is subject to a terminal disclaimer.

(21) Appl. No.: 16/892,638

(22) Filed: Jun. 4, 2020

(65) Prior Publication Data

US 2020/0385798 A1 Dec. 10, 2020

(30) Foreign Application Priority Data

Jun. 4, 2019 (EP) ..................................... 19178107

(51) Int. Cl.
*C12Q 1/68* (2018.01)
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
None
See application file for complete search history.

(56) References Cited

U.S. PATENT DOCUMENTS

| | | | | |
|---|---|---|---|---|
| 2010/0323348 A1* | 12/2010 | Hamady | ............ | C12Q 1/6874 |
| | | | | 536/24.33 |
| 2014/0227705 A1* | 8/2014 | Vogelstein | ........... | C12Q 1/6806 |
| | | | | 435/6.12 |
| 2015/0184214 A1* | 7/2015 | Goodrich | ............... | C12Q 1/686 |
| | | | | 435/194 |
| 2016/0362748 A1 | 12/2016 | Mongan et al. | | |
| 2017/0058339 A1 | 3/2017 | Chee | | |

FOREIGN PATENT DOCUMENTS

WO 2016/010856 A1 1/2016
WO WO-2016010856 A1 * 1/2016 ........... C12Q 1/6869

OTHER PUBLICATIONS

Tian-Hao Zhang et al., "A benchmark study on error-correction by read-pairing and tag-clustering in amplicon-based deep sequencing", BMC Genomics, BioMed Central Ltd., London, UK, vol. 17, No. 1, Feb. 12, 2016, pp. 1-9, XP021233632; Cited in the extended European search report issued on Dec. 16, 2019 in a counterpart Europear patent application.

Extended European search report dated Dec. 16, 2019 in a counterpart European patent application No. 19178107.9.

* cited by examiner

*Primary Examiner* — Suryaprabha Chunduru
(74) *Attorney, Agent, or Firm* — Sughrue Mion, PLLC

(57) ABSTRACT

The present invention relates to a method for determining a nucleotide sequence of a target nucleic acid. The method comprises: providing a pool of amplicons; sequencing each amplicon in the pool of amplicons to obtain sequence information of each amplicon; comparing a part of the sequence information of each amplicon with at least a part of the sequence of the target specific primer section, wherein the part of the sequence information of each amplicon is a sequence starting from position X+1; determining whether the part of the sequence information of each amplicon comprises at least the part of the sequence of the target specific primer section; and determining accurate sequence of the target region using sequence information which comprises at least the part of the sequence of the target-specific primer section.

15 Claims, 20 Drawing Sheets

Specification includes a Sequence Listing.

```
error-free amplicon   3' - CAGTCCTGCAACAT..........GGACAAGGAGGACCTCTCTCGATACT---5'  (SEQ ID NO:1)
short amplicon        3' - CAGTCCTGCAACAT.........GGACAAGGAGGACCTCTCTCGATACT---5'   (SEQ ID NO:2)
long amplicon         3' - CAGTCCTGCAACAT...........GGACAAGGAGGACCTCTCTCGATACT---5' (SEQ ID NO:3)

1....5....10...15....20....25....
sequence information 1: 5' -               ........GTGTCCTCCTGGAGAAGAGCTATGA---3'  (SEQ ID NO:5)
sequence information 2: 5' -              .........GTGTCCTCCTGGAGAAGAGCTATGA---3'  (SEQ ID NO:6)
sequence information 3: 5' -             ..........GTGTCCTCCTGGAGAAGAGCTATGA---3'  (SEQ ID NO:7)
```

Figure 7

| Target nucleic acid ID | Gene name | Target region ID | Target region name | Search sequence | Standard position | |
|---|---|---|---|---|---|---|
| | | | | | lower | upper |
| 1 | XYZ | 1 | exon 1 | CCTGTT | 7 | 12 |
| | | 2 | exon 2 | GTCATC | 7 | 12 |
| | | . | . | . | . | . |
| | | . | . | . | . | . |
| | | . | . | . | . | . |

Figure 13

METHOD FOR ANALYZING NUCLEIC ACID SEQUENCE

TECHNICAL FIELD

In the present specification, a method for analyzing a nucleic acid sequence is disclosed.

BACKGROUND

US 2015/0361492 A1 discloses Safe-Sequencing system, which uses a unique identifier (UID) sequence to identify mutations present in small DNA fragments by a sequencer.

SUMMARY OF THE INVENTION

When analyzing the nucleic acid sequence of a DNA fragment with Next Generation Sequencer (NGS), first, a library of DNA fragments is prepared. Next, from the library, the polynucleotide containing the target region of analysis is obtained. Generally, a tag sequence including a universal primer sequence for binding a sequencing primer, an index sequence for identifying a specimen or the like is added to the polynucleotide.

The addition of a tag sequence to a target sequence can be carried out by PCR using a primer containing the tag or by ligation of the tag.

Sequence information containing the tag is obtained by sequencing, and an error may be contained in the sequence information of the tag portion in some cases. For example, one or more nucleotides are inserted in the tag portion, or one or more nucleotides are deleted. Conventionally, sequence information of leads containing such error is excluded from analysis objects.

An object of the present invention is to improve accuracy of sequence analysis using a sequencer.

Although the sequence information containing an error in the tag portion has been conventionally excluded from the analysis as described above, the target sequence is accurately analyzed even in such sequence, in some cases. In the present invention, the coverage rate (also referred to as "depth", "coverage", "depth of coverage", etc.) of sequencing is improved by also setting sequence information containing an error in the tag portion as an analysis object, and accuracy of sequence analysis is improved.

That is, the present invention provides a method for determining a nucleotide sequence of a target nucleic acid, comprising:

providing a pool of amplicons, wherein the pool of amplicons are prepared by attaching a tag section to a target region in the target nucleic acid by conducting PCR using a tagged primer to prepare a tagged nucleotide and amplifying the tagged nucleotide by PCR using a universal primer which hybridizes to the universal primer section to produce a pool of amplicons, wherein the tagged primer comprises the tag section at the 5' side thereof and a target-specific primer section at the 3' side of the tag section, the tag section comprises a universal primer section at the 5' side thereof and an index section at the 3' side thereof, and the length of the index section is X nucleotides;

sequencing each amplicon in the pool of amplicons to obtain sequence information of each amplicon;

comparing a part of the sequence information of each amplicon with at least a part of the sequence of the target specific primer section, wherein the part of the sequence information of each amplicon is a sequence starting from position X+1;

determining whether the part of the sequence information of each amplicon comprises at least the part of the sequence of the target specific primer section; and determining sequence of the target region using sequence information which comprises at least the part of the sequence of the target-specific primer section.

The present invention further provides a method for determining a nucleotide sequence of a target nucleic acid, comprising:

determining a sequence of a target region by using sequence information obtained from each amplicon in a pool of amplicons, wherein, the amplicon is prepared from template nucleic acids, wherein the template nucleic acid comprises a target region by using a polymerase and a tagged primer;

the tagged primer comprises a tag section at the 5' side thereof and a target-specific primer section at the 3' side of the tag section, wherein the tag section comprises an index section;

the pool of amplicons comprises error-free amplicons, first error amplicons, and second error amplicons, wherein the sequence information derived from the error-free amplicon comprises a complementary sequence to the full length index section at the 3' side thereof and a complementary sequence of the target region at the 5' side thereof, the sequence information derived from the first error amplicon comprises a complementary sequence to a shorter index section at the 3' side thereof and a complementary sequence of the target region at the 5' side thereof, and the sequence information derived from the second error amplicon comprises a complementary sequence to a longer index section at the 3' side thereof and a complementary sequence of the target region at the 5' side thereof, and the sequence of the target region is determined by using sequence information other than sequence information obtained from the first error amplicons.

BRIEF DESCRIPTION OF THE DRAWINGS

FIG. 7 is a diagram showing an outline of primer search.

FIG. 9A is an example in which a target nucleic acid sequencing apparatus and a sequencing apparatus are configured independently. FIG. 9B is an example in which a target nucleic acid sequencing apparatus and a sequencing apparatus are integrated.

FIG. 13 is a diagram showing an example of a search sequence database.

FIG. 15A is an example in which a target nucleic acid sequencing apparatus and a sequencing apparatus are configured independently. FIG. 15B is an example in which a target nucleic acid sequencing apparatus and a sequencing apparatus are integrated.

DETAILED DESCRIPTION OF THE PREFERRED EMBODIMENTS

Abbreviations used in the present specification and drawings have the following meanings.

TR: target region
c-TR: complementary sequence of target region
TS: tag section
u-PS1: 1st universal primer section
i-S: index section
t-PS1: 1st target-specific primer section
u-PS2: 2nd universal primer section
t-PS2: 2nd target-specific primer section
AS1: 1st adaptor section
AS2: 2nd adaptor section

1. Method for Determining Target Nucleic Acid Sequence

A method for determining a target nucleic acid sequence determines a nucleic acid sequence of a target nucleic acid. The method for determining a target nucleic acid sequence can be applied to sequencing using a tag sequence.

A method for determining a target nucleic acid sequence includes a step A of preparing a library of tagged amplicons (hereinafter also simply referred to as "pool of amplicons") containing an amplicon and an amplicon complementary chain using a polynucleotide containing a target region as a template nucleic acid, a step B of sequencing the amplicons, and a step C of determining a sequence of the target nucleic acid.

The method for determining a target nucleic acid sequence may further include a step of outputting sequence information of the target nucleic acid.

In the method for determining a target nucleic acid sequence, when a plurality of target regions is included in the target nucleic acid, a sequence may be determined for all of the plurality of target regions.

Each step will be described in detail below.

[1-1. Step A: Preparation of Pool of Amplicons]

Figure 1:
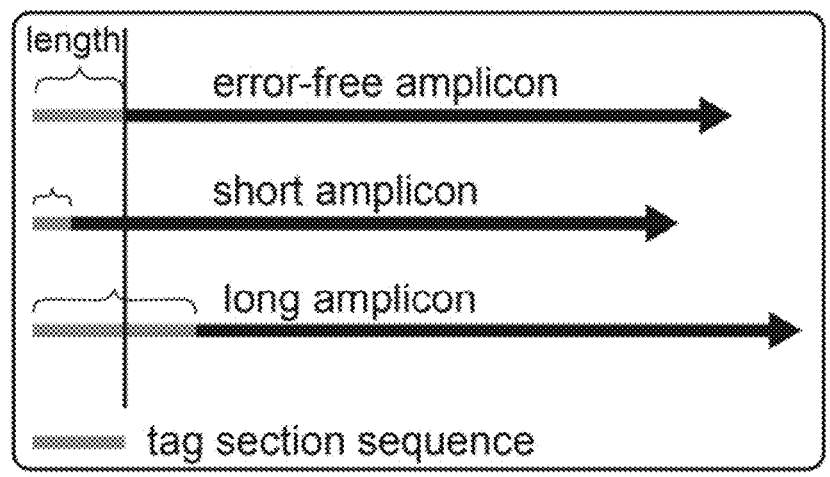
FIG. 1 is a diagram showing an outline of amplicons.

A pool of amplicons may contain the following amplicons as shown in FIG. 1:

an amplicon having an entire sequence of a tag section (error-free amplicon);

an amplicon having a tag section sequence shorter than the length that the sequence of the tag section should have originally (short amplicon); and an amplicon having a tag section sequence longer than the length that the sequence of the tag section should have originally (long amplicon).

The length of the sequence means the number of nucleotides and is expressed in the unit "nt".

The pool of amplicons is prepared using tagged primers. Since tagged primers are set to a predetermined length, the amplicons prepared with the same primer set are ideally all error-free amplicons and all have the same length of nucleotide length. However, tagged primers are usually artificially synthesized before being added to the measurement system, and a synthesis error may occur during the artificial synthesis. A tagged primer shorter than a predetermined length and a tagged primer longer than a predetermined length are unintentionally synthesized by this synthesis error, and these tagged primers containing an error can also be added to the reaction system of the amplicon preparation. The tagged primers containing an error can result in a short amplicon and a long amplicon. During an amplification reaction by polymerase (when preparing a pool of amplicons), an amplification error may occur. That is, deletion of one or more nucleotides or insertion of one or more unnecessary nucleotides may occur in the amplification reaction. This amplification error can result in a short amplicon and a long amplicon.

A target nucleic acid includes a full length or fragment of DNA (derived from genomic DNA, mitochondrial DNA, plasmid DNA, transposon DNA, etc.) to be analyzed, and a full length or fragment of RNA (derived from messenger RNA, ribosomal RNA, transfer RNA, microRNA, non-coding RNA, etc.) to be analyzed. The target nucleic acid may be represented by, for example, a gene name, and may be represented by GENE ID, Accession No., Reference Sequence ID, Chromosome Locus No., Reference SNP (refSNP) Cluster Report ID or the like described in The National Center for Biotechnology Information, or the like.

Preparation of the pool of amplicons is preferably done by PCR. This preparation can be performed by (1) PCR using a tagged primer (tagging and amplification step); or (2) a first PCR using a tagged primer (tagging step) and a second PCR using a universal primer (amplification step).

In the above case (1), at least a tagged primer is used as a primer. PCR may be performed by mixing both a tagged primer and a universal primer with a target nucleic acid. When only a tagged primer is used, the number of PCR cycles is not particularly limited, and it is preferably 10 to 50 cycles, and more preferably 20 to 40 cycles. Prior to the PCR, pre-amplification may be performed using primers not containing a tag section. The primer not containing a tag section may be a primer specific to a target region or may be a random primer.

In the above case (2), at least two PCR reactions are performed. By a first PCR, it is possible to generate a DNA tagged in a target region. After completion of the first PCR, a second PCR can be performed by mixing at least a part of the reaction product, a universal primer, and a polymerase.

The number of first PCR cycles and the number of second PCR cycles are not particularly limited. The number of first PCR cycles is preferably 5 to 20 cycles, and more preferably 10 to 15 cycles. The number of second PCR cycles is preferably 10 to 30 cycles, and more preferably 15 to 25 cycles. Prior to the first PCR, pre-amplification may be performed using primers not containing a tag section. The primer not containing a tag section may be a primer specific to a target region or may be a random primer.

An example of preparing a pool of amplicons using a tagged primer and the like will be specifically described below, with reference to FIGS. 2 to 6.

Figure 2:
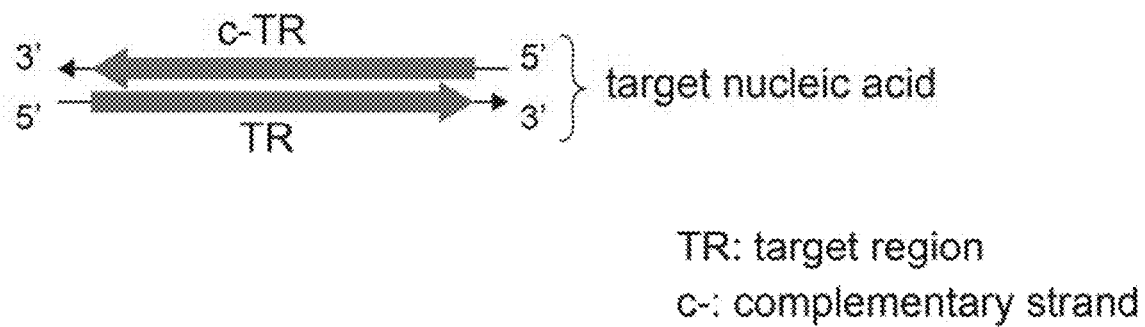
FIG. 2 is a diagram showing an example of a target nucleic acid.

As shown in FIG. 2, the target nucleic acid includes a target region to be subjected to sequence analysis. The target nucleic acid may contain a plurality of target regions. Example in FIG. 2 is a double-stranded polynucleotide comprising a polynucleotide containing a target region and a complementary polynucleotide.

The target nucleic acid can be contained in a DNA extracted from a sample to be analyzed, a DNA library, cDNA obtained by reverse transcription of RNA extracted from the sample to be analyzed, and concentrated and purified DNA thereof. The concentration can be performed by using, for example, KAPA Hyper Prep Kit (NIPPON Genetics Co, Ltd), SureSelect target enrichment system (Agilent Technologies, Inc.), or the like.

Figure 3:
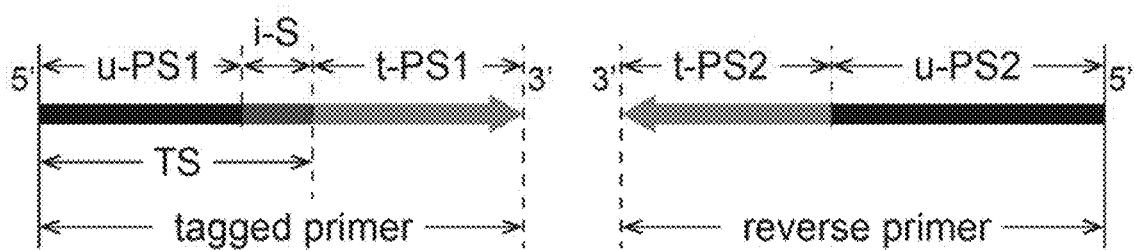
FIG. 3 is a diagram showing an example of a configuration of a tagged primer for preparing a tagged daughter molecule.

FIG. 3 shows an example of a configuration of a tagged primer for preparing a tagged daughter molecule and an example of a configuration of a reverse primer. The tagged primer contains a tag section (TS) on the 5' side and a 1st target-specific primer section (t-PS1) on the 3' side. t-PS1 has the same sequence as a part of the sequence on the 5' side of the target sequence.

The length of the tag section sequence is not particularly limited, and it is 20 to 100 nt, and preferably 30 to 50 nt. The tag section contains an index section. The tag section may contain a 1st universal primer section (u-PS1) on the 5' side of the index section. The tagged primer shown in FIG. 3 is an example containing a 1st universal primer section, an index section and a 1st target-specific primer section, in order from the 5' terminal.

The reverse primer contains a 2nd target-specific primer section (t-PS2). The reverse primer may contain a 2nd universal primer section (u-PS2) and the like on the 5' side of t-PS2. The reverse primer in FIG. 3 is an example containing u-PS2 and t-PS2 in order from the 5' side. t-PS2 has a sequence complementary to a part of the sequence on the 3' side of the target sequence.

The index section contains a sequence for identifying the origin of the amplicon. The index section can be inserted or added to the tagged primer. The index section may be inserted or added to the reverse primer. For example, it is possible to assign index sections of different sequences for each individual. In this case, sequence analysis can be performed by mixing the amplicon obtained from the target sequence of the individual A and the amplicon obtained from the target sequence of the individual B. Index sections of different sequences may be assigned for each specimen. In this case, sequence analysis can be performed by mixing the amplicon obtained from the target sequence of the specimen A and the amplicon obtained from the target sequence of the specimen B. In either case, an index of a predetermined sequence is used.

It is also possible to assign different indices for each molecule of the target nucleic acid contained in the sample. In this case, it is possible to identify from which molecule the sequence of the amplicon is derived. In this case, the sequence of indices is preferably a random sequence and may be a unique identifier (UID) as described in US 2015/0361492 A. US 2015/0361492 A1 is incorporated herein by reference.

The universal primer section may be a section containing the same sequence as the universal primer used for sequencing. The "universal primer" is a primer capable of amplifying an amplicon, regardless of the sequence of the index section and the sequence of the target nucleic acid. As a sequence of the universal primer section, a known sequence can be used, and example thereof includes a sequence derived from M13 phage. The index section is a section containing a sequence for identifying each amplicon, and preferably a sequence not present in the target region or the universal primer section.

The length of the universal primer section sequence is not particularly limited, and it is about 5 to 20 nt. The length of the index section sequence is not particularly limited, and it is about 4 to 30 nt. The length of the index section sequence can be selected from the range consisting of, for example, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, or 30 nt. The length of the index section sequence is represented by "X" in some cases. X is a positive integer.

When the nucleotide length of the index sequence of the error-free amplicon is X nt, the nucleotide length of the index sequence of the short amplicon is (X−1) nt or less, the nucleotide length of the index sequence of the long amplicon is (X+1) nt or more. The index sequence of the short amplicon can be (X−25) nt or more and (X−1) nt or less. The index sequence of the long amplicon can be (X+1) nt or more and (X+40) nt or less.

The length of the target-specific primer section sequence is not limited as long as it can be annealed with a template nucleic acid. For example, the length of the target-specific primer section sequence is about 5 to 50 nt, and preferably about 10 to 30 nt. The length of the target-specific primer section sequence is expressed as "m" in some cases. m is a positive integer. The target-specific primer section sequence need not be perfectly complementary to the target sequence as long as it hybridizes to the target nucleic acid and functions as a primer. For example, the target-specific primer section sequence may not be complementary to the target sequence, by about 1 nt, 2 nt, or 3 nt.

Figure 4:
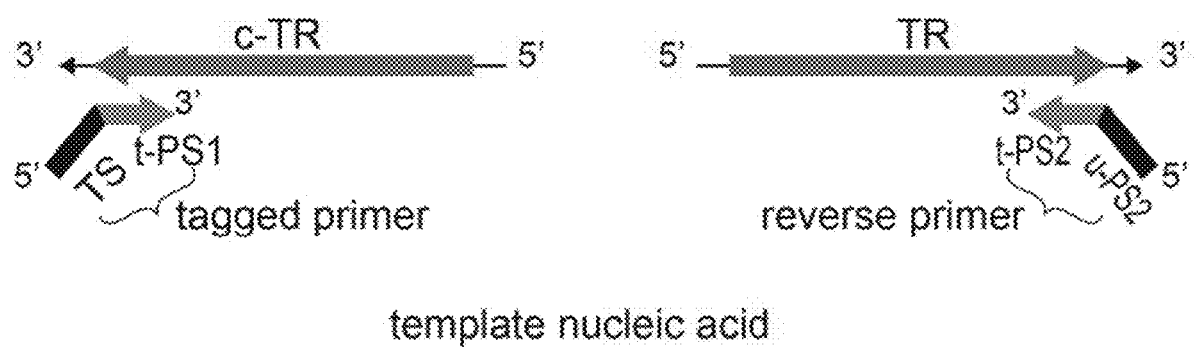
FIG. 4 is a diagram showing an example of annealing of a target nucleic acid with a tagged primer and a reverse primer.

FIG. 4 is a diagram showing an example of annealing of a target nucleic acid with a tagged primer and a reverse primer. The tagged primer that functions as a forward primer hybridizes to c-TR and the reverse primer hybridizes to TR. After annealing, an elongation reaction can be carried out using DNA polymerase according to a known method.

Figure 5:
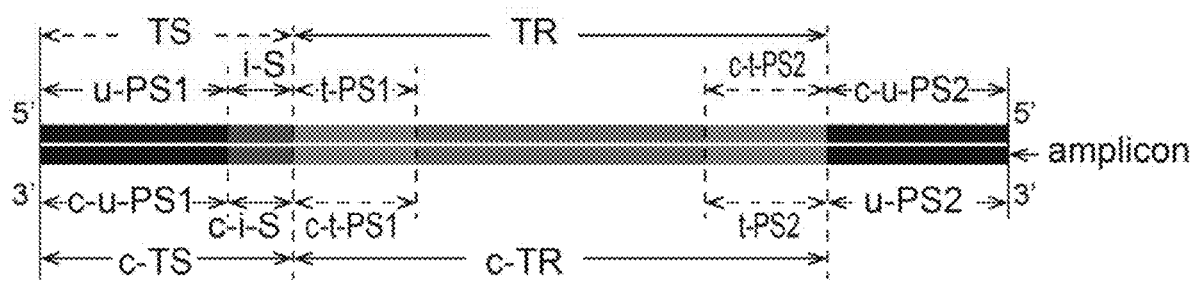
FIG. 5 is a diagram showing an example of a structure of amplicons generated by an elongation reaction.

An example of a structure of amplicons generated by the elongation reaction is shown in FIG. 5. A pool of amplicons is prepared by amplifying a daughter molecule, for example, by PCR method. Generally, an amplicon is in a double-stranded state in which it is bound to a complementary strand.

In this example, the amplicon is a lower strand shown in FIG. 5. The amplicon contains c-u-PS1, c-i-S, c-TR and u-PS2 from the 3' side. c-t-PS1 and t-PS2 are located in c-TR. The amplicon complementary strand contains u-PS1, i-S, TR, and c-u-PS2 from the 5' side. t-PS1 and c-t-PS2 are located in TR.

As described above, due to a synthesis error of tagged primer, PCR amplification error or the like, the pool of amplicons is not only an error-free amplicon, but also a long amplicon containing c-TS longer than a predetermined length and a short amplicon containing c-TS shorter than the predetermined length. When the error is present in u-PS1, amplification by a universal primer is inhibited and becomes inefficient, so that an amplicon containing long u-PS1 or short u-PS1 is unlikely to occur. On the other hand, when the error exists in i-S, amplification by the universal primer is not inhibited. Thus, the short amplicon contained in the pool of amplicons is an amplicon primarily having short c-i-S, and the long amplicon is an amplicon primarily having long c-i-S.

Figure 6:
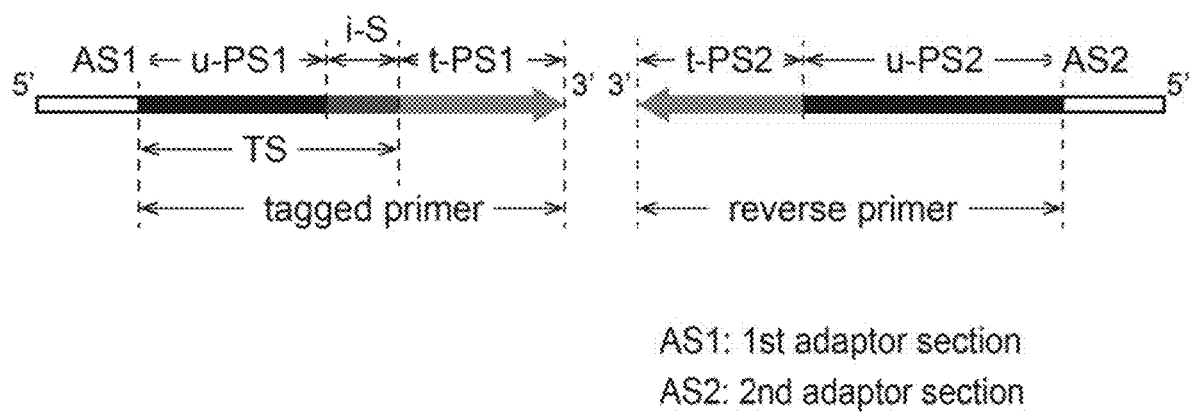
FIG. 6 is a diagram showing another example of a tagged primer and a reverse primer.

Another example of a tagged primer and a reverse primer is shown in FIG. 6. This tagged primer contains a 1st adaptor section (AS1) on the 5' terminal side. The tagged primer can be used to immobilize the amplicon to a solid phase. The reverse primer contains a 2nd adaptor section (AS2) on the 5' side. These adaptor sections are used when sequencing of amplicons is performed on a solid phase (flow cell, bead, etc.). For example, a sequence complementary to the adaptor section can be immobilized on the solid phase in advance. An amplicon prepared using a primer containing an adaptor section has adaptor sections at both ends thereof, so that the amplicon can be immobilized on the solid phase. Amplicon synthesis using a primer containing an adaptor section is the same as FIG. 2 to FIG. 5, except that the adaptor sections are added to the terminals.

[1-2. Step B: Sequencing]

In step B, the amplicon is sequenced. Sequence information (read) of the target region is obtained by this sequencing. The sequence information is information obtained by converting detected fluorescence signals, ions or the like as information indicating each nucleotide in a sequencer into nucleotide information of A, G, T and C, respectively, and arranging them in order of detection (ascending order). Normally, the sequence information is obtained from the 5' side. The sequencer is not limited as long as sequence information can be obtained from the amplicon, and a known device can be used. The sequencer is preferably a next generation sequencer, for example. Examples of the next generation sequencer include MiSeq9 (registered trademark), HiSeq (registered trademark), NextSeq (registered trademark), MiSeq (registered trademark) of Illumina Inc. (San Diego, Calif.); Ion Proton (registered trademark), Ion PGM (registered trademark) of Thermo Fisher Scientific, Inc. (Waltham, Mass.); GS FLX+ (registered trademark) and GS Junior (registered trademark) of F. Hoffmann-La Roche, Ltd. (Basel, Switzerland); and the like.

For example, a sequencer of Illumina Inc. can amplify polynucleotides of enormous numbers of target regions on a flow cell by combining Bridge PCR method and Sequencing-by-synthesis method and perform sequencing of the amplification product.

A universal primer that binds c-u-PS1 can be used as a sequencing primer. According to this, it is possible to obtain information of sequences containing i-S and TR. Information of sequences containing c-TR and c-i-S can also be obtained using a universal primer that binds to c-u-PS2. Ideally, the tagged primer does not contain a synthesis error, no PCR amplification error occurs, and no sequencing error occurs, so sequence information of i-S and TR of error-free amplicons can be obtained. When a tagged primer containing a synthesis error or the like is used, sequence information of an amplicon (Short amplicon) containing i-S and TR shorter than a predetermined length X and sequence information of an amplicon (Long amplicon) containing i-S and TR longer than a predetermined length X are obtained.

[1-3. Step C: Determination of Sequence of Target Region]

In step C, the accurate sequence of the target region is determined using the sequence information obtained from an error-free amplicon and the sequence information obtained from a long amplicon, among the sequence information obtained in step B above. The short amplicon is not used to determine the accurate sequence. In other words, the step of discriminating amplicons described below can also be referred to as a step of omitting sequence information that is not used for determining the accurate sequence of the target region.

<Discrimination of Amplicons>

It is possible to determine by the following method which sequence of error-free amplicon, long amplicon or short amplicon is represented by the obtained sequence information.

When the t-PS sequence or the 5' terminal side partial sequence of t-PS1 is contained from the (X+1)th or later counted from the 5' side of the sequence information obtained by sequencing, it is an error-free amplicon or a long amplicon. On the other hand, when a part or all of the sequence of t-PS1 is not contained in the (X+1)th and subsequent sequence of the obtained sequence information, it is a short amplicon. Therefore, preferably, the obtained sequence information is firstly compared with the sequence of t-PS1 to search for the presence or absence of the sequence of t-PS1 (also referred to as "primer search"). Next, only the sequence information in which the sequence of t-PS1 is present is used for determining the accurate sequence. When the obtained sequence information does not contain the sequence of t-PS1, the sequence information is not used for determining the accurate sequence. The length of the 5' terminal side partial sequence of t-PS1 is not particularly limited. The length of the 5' terminal side partial sequence of t-PS1 is preferably 4 nt or more, and more preferably 6 nt or more (in the example of FIG. 7, the length of the 5' terminal side partial sequence of t-PS1 is 6 nt).

The primer search will be described with reference to FIG. 7 as an example. In FIG. 7, SEQ ID NOs: 1 to 3 represent an error-free amplicon, a short amplicon, and a long amplicon, respectively. Each amplicon contains a complementary sequence section to the universal primer section (c-u-PS1: black frame), a complementary sequence section to the index section (c-i-S: dark gray frame), and a complementary sequence of target region (c-TR). The 3' side of the complementary sequence of the target region is a complementary sequence of target-specific primer section (c-t-PS1: light gray frame). Nucleotide number 1 is a nucleotide firstly detected in sequencing. In sequence information 1 to 3 (SEQ ID NOs: 4 to 6), a repetitive sequence of "n" in a dark gray frame means a complementary sequence of the sequence information of the index section indicated by repeat of "N" of SEQ ID NOs: 1 to 3. "CCTGTTCCTCCCTGG (SEQ ID NO: 7)" in the light gray frame is a partial sequence of the target-specific primer section. Moreover, "CCTGTT" surrounded by a square frame is a sequence (search sequence) of a predetermined region. In this example, the search sequence is the 5' terminal side partial sequence of t-PS1.

In FIG. 7, sequence information 1 to 3 (SEQ ID NOs: 4 to 6) are sequence information derived from different amplicons obtained in step B. SEQ ID NO: 4 is sequence information derived from an amplicon of SEQ ID NO: 1, SEQ ID NO: 5 is sequence information derived from an amplicon of SEQ ID NO: 2, and SEQ ID NO: 6 is sequence information derived from an amplicon of SEQ ID NO: 3. "n" in SEQ ID NOs: 4 to 6 means a complementary sequence of the sequence indicated by repeat of "N" of SEQ ID NOs: 1 to 3. Since the sequence is carried out with a primer having the sequence of u-PS1, the complementary sequence of c-u-PS1 is not contained in SEQ ID NOs: 4 to 6. Since the i-S is theoretically 14 nt, nucleotides up to 14th (X=14) from the 5' terminal of each sequence information are excluded for each sequence information, further whether the search sequence is present in the first and subsequent sequence information is detected, and whether or not each sequence information is used for accurate sequence determination is determined. In FIG. 7, a solid black line is drawn between the 14th and 15th nucleotides from the 5' terminal of the sequence information, and the arrow direction from the solid line indicates the sequence to be searched for the search sequence (the 15th and subsequent nucleotides of each sequence). In sequence information 1 and 3 (SEQ ID NOs: 4 and 6), since all of the search sequence "TTCCTC" is continuously detected in the arrow direction from the solid black line, it is determined that the entire sequence of the search sequence is present. It can be determined that sequence information 1 and 3 (SEQ ID NOs: 4 and 6) is derived from an error-free amplicon or a long amplicon, respectively. In sequence information 3 (SEQ ID NO: 6), since a part of the search sequence is missing, it is determined that the entire sequence of the search sequence is not present. Therefore, it can be determined that sequence information 2 (SEQ ID NO: 5) is derived from a short amplicon.

The 1st to Xth sequence of the sequence information derived from a short amplicon contains a partial sequence at the 5' terminal of TR. Upon analysis, even the sequence information derived from a short amplicon is recognized as an index sequence from the 1st to Xth sequence from the 5' terminal side, so that it is not possible to form a family that shares the same index. Since the sequence of the target region is determined to be (X+1)th or later, the sequence of the analyzed target region has a deletion of a part of the 5' terminal side compared to the sequence of the accurate target region. When such a sequence is used for sequencing, accuracy of sequence analysis of the target region may be reduced. On the other hand, the sequence of the target region analyzed from a long amplicon does not have a deletion compared to the accurate sequence. By using the sequence of the target region analyzed from a long amplicon, the number of sequence information used for sequencing increases. As a result, it is considered that the depth of coverage is improved and the reliability of analysis result is improved.

Sequence information that can be used to determine the accurate sequence of the target region to be performed in the next step is selected by primer search.

<Determination of Accurate Sequence of Target Region>

Next, the accurate sequence of the target region is determined, from the sequence information obtained from an error-free amplicon and the sequence information obtained from a long amplicon. In other words, the accurate sequence of the target region is determined, using sequence information other than the sequence information obtained from a short amplicon.

Changes (errors) in nucleotide sequence caused by in vitro manipulations such as PCR and sequencing are generally referred to as PCR errors or sequencing errors, and are sequences not present in the sequence of the target nucleic acid as a template.

In this step, whether the sequence information obtained from an error-free amplicon or the sequence information obtained from a long amplicon reflects the sequence of the target nucleic acid, that is, whether the sequence of the target region is an accurate sequence is determined.

Whether the sequence of the target region is an accurate sequence can be discriminated by, for example, the technique of US 2015/0361492 A1.

Specifically, the origin of each amplicon can be identified by the index sequence contained in the sequence information as described in the above 1-1. As exemplified in FIG. 8, when the above-described UID is used as an index sequence, daughter molecules to which different UID sequences for each target nucleic acid are added are prepared from the target region of multiple copies of target nucleic acids (in this example, there is one type of target region contained in the target nucleic acid) present in a DNA sample (FIG. 8: Step A1). Next, the daughter molecules to which the UID sequence is added are amplified by PCR using a universal primer to prepare a pool of amplicons (FIG. 8: Step A2). The pool of amplicons prepared as above contains amplicons amplified using each daughter molecule to which the UID sequence is added as a template. Step A shown in FIG. 8 corresponds to step A described in the above 1-1.

Next, sequencing of each amplicon is performed. Step B shown in FIG. 8 corresponds to step B described in the above 1-2.

The sequence information derived from the amplicons amplified from one molecule of daughter molecule to which the UID sequence is added has all the same UID sequence. A group of amplicons having the same UID sequence is referred to as "family", and an individual amplicon having the same UID sequence is referred to as "member".

Next, the sequence to be used for determining the accurate sequence of the target sequence is selected according to the method described in the <Discrimination of Amplicons> with regards to the length of amplicons. Step C1 shown in FIG. 8 corresponds to the step described in the <Discrimination of Amplicons>.

Next, whether or not the sequence of the target region is an accurate sequence is determined using the sequence information selected in the step of discrimination of amplicons.

In this step, first, comparison (alignment) of sequence information is made within this same family. By this alignment, a nucleotide showing a consensus rate of not less than a predetermined value in each position in the sequence information is determined as a nucleotide of the target region. This determination is performed at all positions of the sequence information, and an accurate sequence of entire sequence of the target region is determined. By doing like this, PCR errors, sequencing errors and the like are eliminated. It is because PCR errors, sequencing errors and the like are generally 0 to several % within the family, and hardly become majority within the family.

The predetermined value may be 1%, 5%, 10%, 20%, 30%, 40%, 50%, 60%, 70%, 80%, or 90%. The predetermined value is preferably 80% or 90%.

Figure 8:
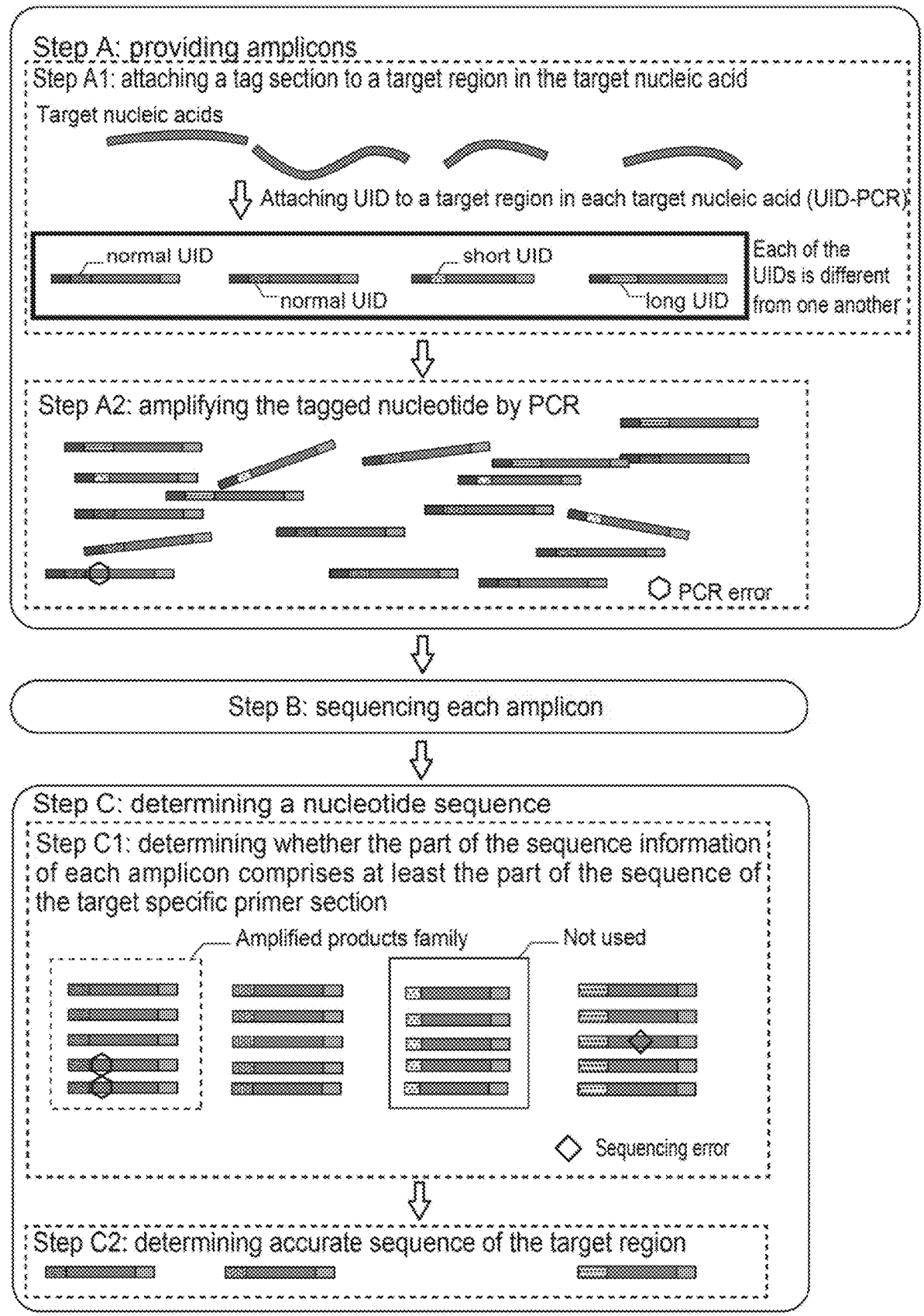
FIG. 8 shows features of Safe-Sequencing technology.

In step C2 of FIG. 8, sequence information obtained from families of error-free amplicons and long amplicons is used for accurate sequence determination. Sequence information obtained from a family of short amplicons is not used to determine an accurate sequence.

[1-4. Mutation Detection Method]

The method for determining a target nucleic acid sequence may include a mutation detection step D in addition to the above steps A to C. In the present specification, the term "mutation" refers that a specific base in the wild-type sequence is replaced with another base in vivo.

In step D, a reference sequence and the sequence information of each family analyzed in step C are compared. The reference sequence may be a wild-type sequence of the target region. When a nucleotide different from the reference sequence is present in the sequence of a part of family, this sequence can be determined to be derived from mutant DNA in a sample. In this case, it can be determined that the sample DNA contains a mutation. In the absence of a nucleotide different from the reference sequence, it can be determined that the sample DNA does not contain a mutation.

As the reference sequence, a sequence registered in the public sequence information database can be used. As the public sequence information database, NCBI RefSeq (web page, ncbi.nlm.nih.gov/refseq/), NCBI GenBank (web page, ncbi.nlm.nih.gov/genbank/), UCSC Genome Browser, and the like. As the reference sequence, a sequence registered in a publicly known mutation information database may be used. Examples of publicly known mutation information databases include COSMIC database (web page, sanger-.ac.uk/genetics/CGP/cosmic/), ClinVar database (web page, ncbi.nlm.nih.gov/clinvar/), db SNP (web page, ncbi.nlm-.nih.gov/SNP/), HapMap Genome Browser release #28, Human Genetic Variation Browser (web page, genome.med-.kyoto-u.ac.jp/SnpDB/index.html), and 1000 Genomes (web page, 1000genomes.org/).

The result of sequence analysis may be outputted. The output method is not particularly limited, and, for example, the analysis result may be displayed on a monitor of a sequencing apparatus, transmitted to another terminal, or printed out on paper. When a mutation detection result is outputted, the presence or absence of a mutation may be outputted. When there is a mutation, an explanation of the analysis result on the mutation (type of mutation, site of mutation, etc.) may be added.

2. Target Nucleic Acid Sequencing Apparatus

[2-1. First Target Nucleic Acid Sequencing Apparatus]
[2-1-1. Hardware Configuration]

The target nucleic acid sequencing apparatus 10 includes at least a processing unit 101 and a storage unit. The storage unit is configured by a main storage unit 102 and/or an auxiliary storage unit 104. The target nucleic acid sequencing apparatus 10 may be an apparatus for realizing the method stated in the claims or the above 1. In the explanation of the target nucleic acid sequencing apparatus 10 and the operation of the target nucleic acid sequencing apparatus 10, the description of the above 1 is incorporated herein for terms common to the terms described in the above 1.

The processing unit 101 determines the sequence of the target region.

Figure 9A:
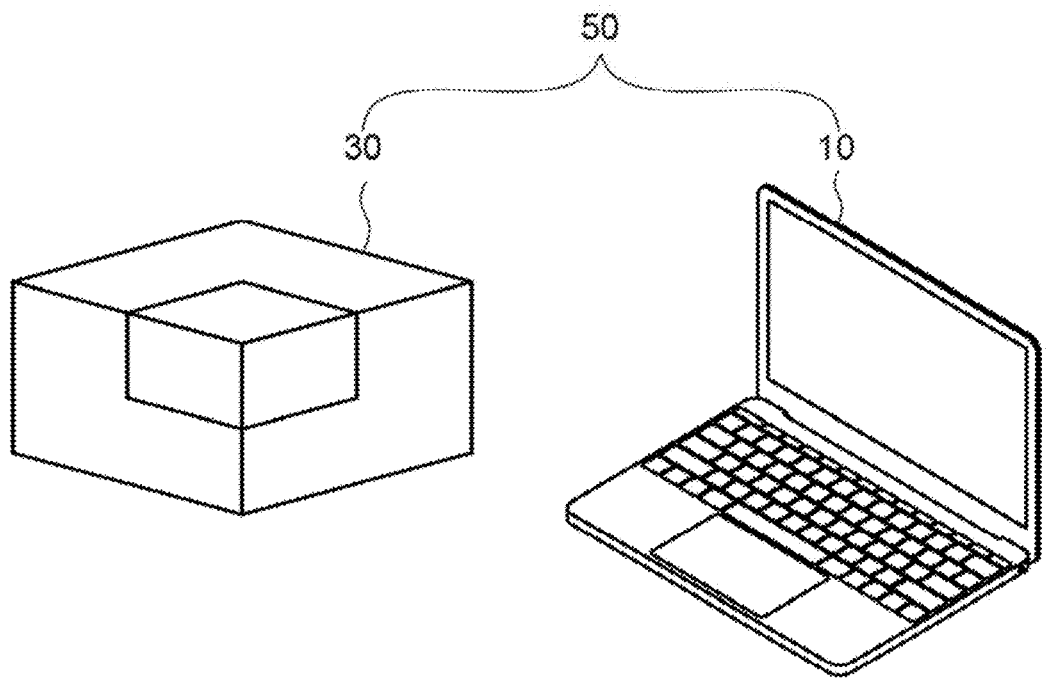
FIGS. 9A and 9B are diagrams showing a configuration of a first target nucleic acid sequencing apparatus.
Figure 9B:
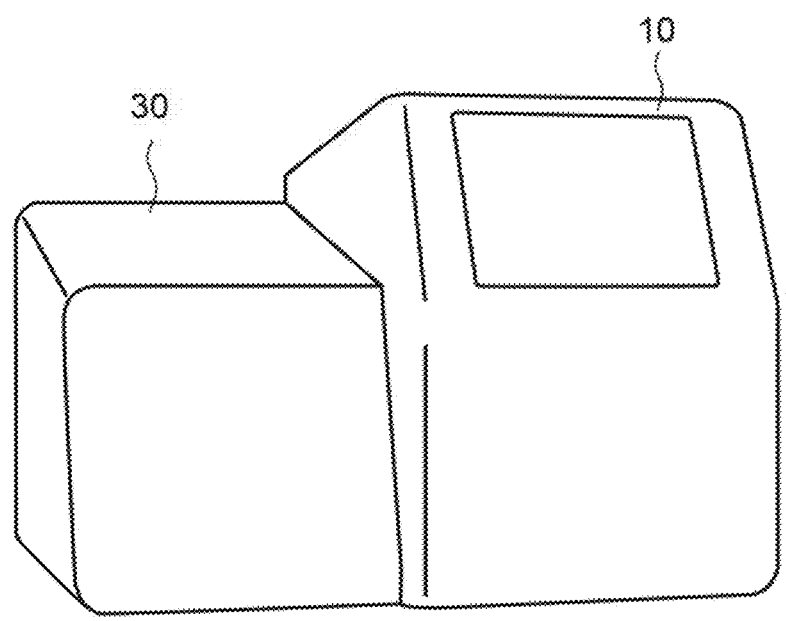
Figure 10:
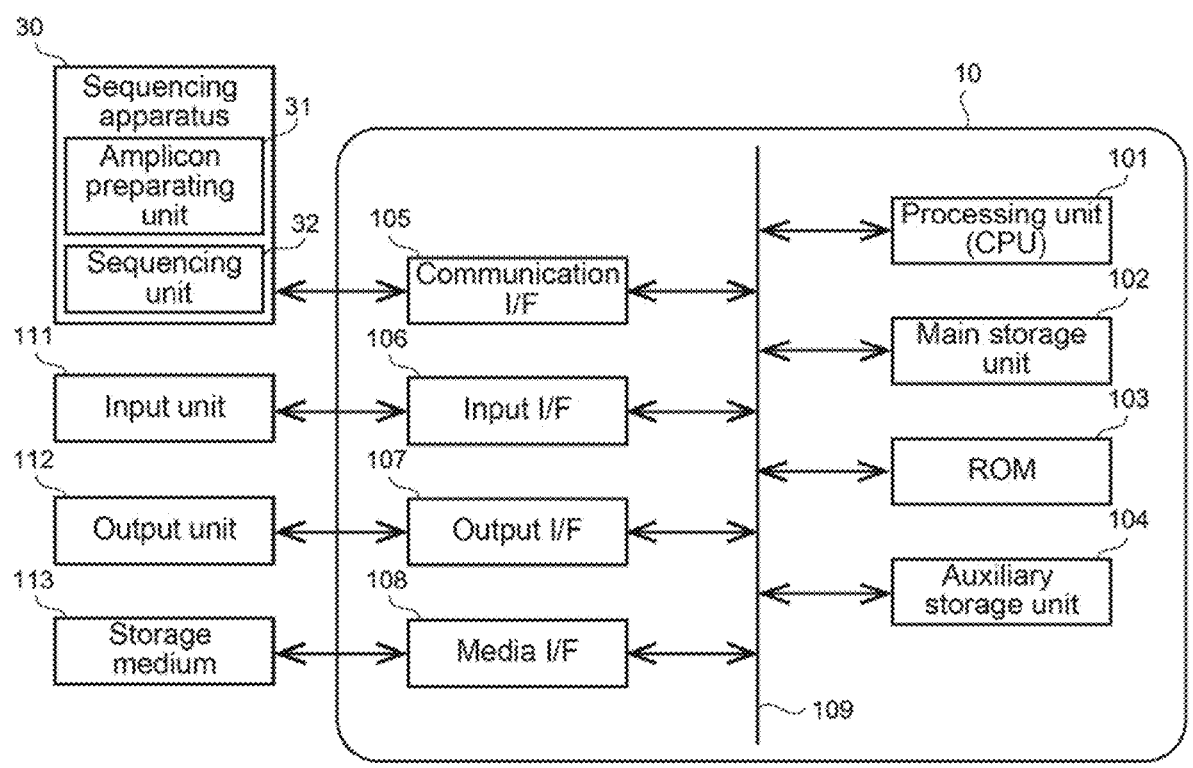
FIG. 10 is a diagram showing an outline of a hardware configuration of a first target nucleic acid sequencing apparatus.

FIG. 9 and FIG. 10 show the configuration of the target nucleic acid sequencing apparatus 10. The target nucleic acid sequencing apparatus 10 may be connected to an input unit 111, an output unit 112, and a storage medium 113. The target nucleic acid sequencing apparatus 10 may be connected to a sequencing apparatus 30 that performs sequencing. The target nucleic acid sequencing apparatus 10 may constitute a target nucleic acid sequence sequencing system 50 connected to the sequencing apparatus 30 directly or via a network or the like (FIG. 9A). The target nucleic acid sequencing apparatus 10 and the sequencing apparatus 30 may be integrated as shown in FIG. 9B.

As shown in Table 10, in the target nucleic acid sequencing apparatus 10, a processing unit 101, a main storage unit 102, a ROM (read only memory) 103, an auxiliary storage unit 104, a communication interface (I/F) 105, an input interface (I/F) 106, an output interface (I/F) 107 and a media interface (I/F) 108 are data-communicably connected with each other via a bus 109.

The processing unit 101 is configured by a CPU, an MPU, a GPU, or the like. The processing unit 101 executes a computer program stored in the auxiliary storage unit 104 or the ROM 103 and processes data to be obtained so that the target nucleic acid sequencing apparatus 10 functions.

The ROM 103 is configured by a mask ROM, a PROM, an EPROM, an EEPROM and the like, and a computer program executed by the processing unit 101 and data used for the computer program are recorded in the ROM 103. When starting the target nucleic acid sequencing apparatus 10, the ROM 103 stores a boot program executed by the processing unit 101 and programs and settings related to the operation of hardware of the target nucleic acid sequencing apparatus 10.

The main storage unit 102 is configured by a RAM (Random Access Memory) such as SRAM or DRAM. The main storage unit 102 is used for reading the computer program recorded in the ROM 103 and the auxiliary storage unit 104. The main storage unit 102 is used as a work area when the processing unit 101 executes these computer programs.

The auxiliary storage unit 104 is configured by a semiconductor memory element such as a hard disk and a flash memory, an optical disk, and the like. In the auxiliary storage unit 104, various computer programs to be executed by the processing unit 101, such as operating systems and application programs, and various setting data used for executing computer programs are stored. The auxiliary storage unit 104 stores the sequences of the tagged primer and each section constituting the tagged primer, the length of the tagged primer and each section constituting the tagged primer, the search sequence, the standard position of the search sequence, the sequence of predetermined regions, the predetermined value of the consensus rate, and the like. The auxiliary storage unit 104 may store the sequence information obtained from the sequencing apparatus 30. The auxiliary storage unit 104 may store reference sequences and the like obtained via the network. The auxiliary storage unit 104 may store a computer program for performing a primer search of a nucleotide sequence.

The communication I/F 105 is configured by serial interfaces such as USB, IEEE1394 and RS-232C, parallel interfaces such as SCSI, IDE and IEEE1284, an analog interface including a D/A converter and an A/D converter, a network interface controller (Network interface controller: NIC), and the like. Under the control of the processing unit 101, the communication I/F 105 receives the data from the sequencing apparatus 30 or another external device, and the communication I/F 105 transmits or displays information stored in or generated by the target nucleic acid sequencing apparatus 10 as necessary to the sequencing apparatus 30 or to the outside. The communication I/F 105 may communicate with the sequencing apparatus 30 or another external device (not shown, for example, another computer, or a cloud system) via a network.

The input I/F 106 is configured by, for example, serial interfaces such as USB, IEEE1394 and RS-232C,s parallel interfaces such as SCSI, IDE and IEEE1284, an analog interface including a D/A converter an A/D converter, and the like. The input I/F 106 receives character input, click, voice input and the like from the input unit 111. The received input content is stored in the main storage unit 102 or the auxiliary storage unit 104.

The input unit 111 is configured by a touch panel, a keyboard, a mouse, a pen tablet, a microphone, and the like. The input unit 111 performs character input or voice input to the target nucleic acid sequencing apparatus 10. The input unit 111 may be connected from outside the target nucleic acid sequencing apparatus 10 or integrated with the target nucleic acid sequencing apparatus 10.

The output I/F 107 is configured by, for example, the same interface as the input I/F 106. The output I/F 107 outputs the information generated by the processing unit 101 to the output unit 112. The output I/F 107 outputs the information generated by the processing unit 101 and stored in the auxiliary storage unit 104, to the output unit 112.

The output unit 112 is configured by, for example, a display, a printer, and the like. The output unit 112 displays the measurement results transmitted from the sequencing apparatus 30, various operation windows in the target nucleic acid sequencing apparatus 10, analysis results, and the like.

The media I/F 108 reads, for example, application software or the like stored in the storage medium 113. The read application software or the like is stored in the main storage unit 102 or the auxiliary storage unit 104. The media I/F 108 writes the information generated by the processing unit 101 in the storage medium 113. The media I/F 108 writes the information generated by the processing unit 101 and stored in the auxiliary storage unit 104 to the storage medium 113.

The storage medium 113 is configured by a flexible disk, CD-ROM, DVD-ROM, or the like. The storage medium 113 is connected to the media I/F 108 by a flexible disk drive, a CD-ROM drive, a DVD-ROM drive, or the like. In the storage medium 113, an application program or the like for allowing the computer to execute operation may be stored.

The processing unit 101 may obtain application software and various settings necessary for controlling the target nucleic acid sequencing apparatus 10 via a network, instead of reading from the ROM 103 or the auxiliary storage unit 104. The application program is stored in the auxiliary storage unit of the server computer on the network, and it is also possible that the target nucleic acid sequencing apparatus 10 accesses the server computer to download the computer program and store it in the ROM 103 or the auxiliary storage unit 104.

In the ROM 103 or the auxiliary storage unit 104, an operation system for providing a graphical user interface environment such as Windows (registered trademark) manufactured and sold by Microsoft Corporation is installed. It is assumed that the application program according to the second embodiment operates on the operating system. That is, the target nucleic acid sequencing apparatus 10 may be a general-purpose computer such as a personal computer.

[2-1-2. Configuration of Sequencing Apparatus]

The sequencing apparatus 30 is not limited as long as it can analyze a nucleotide sequence. As shown in FIG. 10, the sequencing apparatus 30 may further include an amplicon preparing unit 31 in addition to a sequencing unit 32. The sequencing apparatus 30 is preferably a next generation sequencer. Examples of the next generation sequencer include the device described in the above 1-2.

[2-1-3. Operation of First Target Nucleic Acid Sequencing Apparatus]

An example of the operation of the target nucleic acid sequencing apparatus 10 will be described with reference to FIG. 11. The following operations are processed by the processing unit 101 according to a computer program to be described later.

The processing unit 101 obtains sequence information obtained by the sequencing apparatus 30, for example, in accordance with an instruction to start processing inputted from the input unit 111 by the user (Step S20). At this time, for example, when reading sequence information by input from the input unit 111 by the user, or from the sequencing apparatus 30, the processing unit 101 obtains an identification number (subject ID) for identifying a subject from whom a sample was obtained, a sample identification ID for identifying the type (blood, tissue, formalin fixed/paraffin embedded (FFPE) tissue) of sample, an identification number (target nucleic acid identification ID) for identifying a target nucleic acid, an identification number (target region identification ID) for identifying a target nucleic acid, and the like. The obtained sequence information, identification ID and the like are stored in the main storage unit 102 and/or the auxiliary storage unit 104.

Figure 12:
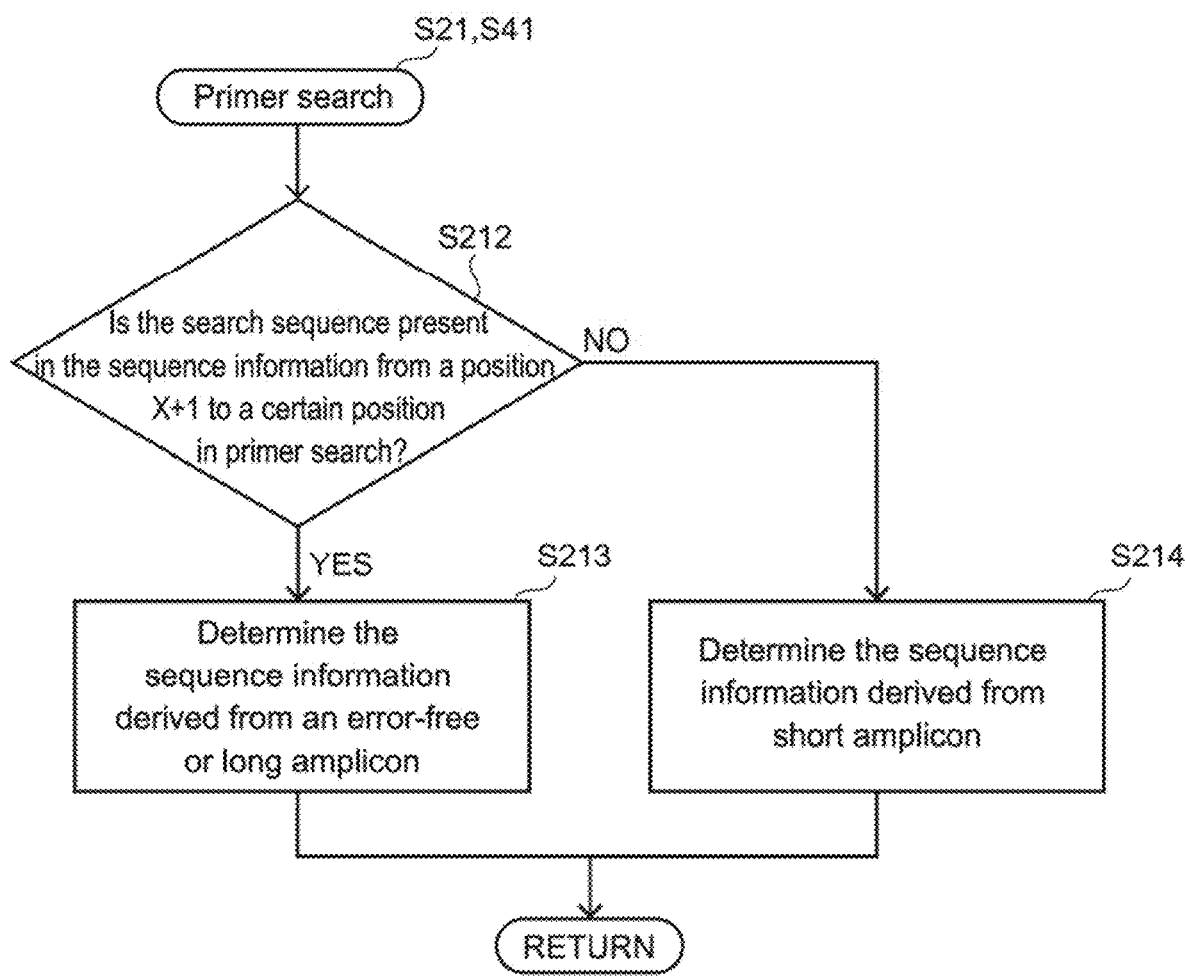
FIG. 12 is a flowchart showing an example of selection processing of sequence information used in the first target nucleic acid sequencing apparatus.

In accordance with the method described in the above 1-2., the processing unit 101 discriminates whether or not each sequence information obtained in Step S20 can be used for determining the accurate sequence of the target sequence, by the primer search described in the above 1-3. (Step S21). A specific flow of Step S21 is shown in FIG. 12, and described later.

In Step S21, the processing unit 101 determines the sequence discriminated to be usable for determining the accurate sequence of the target sequence, that is, the accurate sequence of the target region, based on the sequence information other than sequence information of short amplicon (sequence information of error-free amplicon and sequence information of long amplicon) (Step S22). A method for determining the accurate sequence of the target region will be described later with reference to FIG. 19.

Next, the processing of the processing unit 101 in the primer search shown in Step S21 will be described with reference to FIG. 12.

For the obtained sequence information, the processing unit 101 arranges each nucleotide in each sequence information in the order in which they are detected (Step S211). At this time, a nucleotide number is assigned to each nucleotide in ascending order with the first detected nucleotide being the smallest number (for example, "1").

Figure 11:
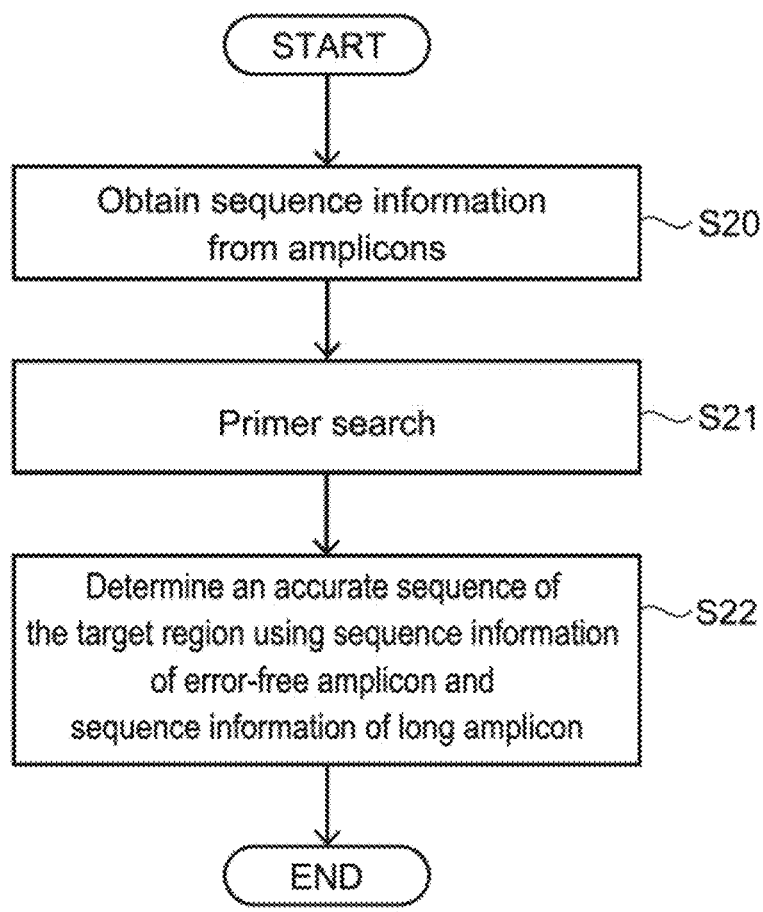
FIG. 11 is a flowchart showing an example of processing of the first target nucleic acid sequencing apparatus.

Based on the target region identification ID and the like of the sequence information obtained in Step S20 shown in FIG. 11, the processing unit 101 reads the sequence of a search sequence corresponding to the obtained sequence information, from sequences of a plurality of search sequences stored in the auxiliary storage unit 104, for example, as a search sequence database (FIG. 13) and the standard position thereof. In addition to the sequence of the search sequence and the standard position, the search sequence database may contain a target nucleic acid identification number (target nucleic acid ID), a gene name, a target region identification number (target region ID), a target region name, or the like. The search sequence database may be grouped for each panel (set) of genes to be analyzed. The search sequence database may be stored in the auxiliary storage unit 104, or it may be obtained at the time of determining the sequence via a network.

The processing unit 101 searches for a sequence that is substantially the same as the sequence of the predetermined region (hereinafter referred to as "search sequence") read from the auxiliary storage unit 104 with respect to the obtained sequence information. In this search, when the length of the index section sequence is X, the processing unit 101 searches whether or not there is substantially the same sequence as the search sequence in the (X+1)th and subsequent sequence information of the obtained sequence information.

The processing unit 101 determines whether or not there is the same sequence as the search sequence in the (X+1)th and subsequent sequence information of the obtained sequence information (Step S212). When it is determined to be "present" (YES), it is determined that the obtained sequence information is derived from an error-free amplicon or a long amplicon (Step S213). Alternatively, instead of determining that the obtained sequence information is derived from an error-free amplicon or a long amplicon in Step S213, it may be determined that the obtained sequence information is used in Step S22 shown in FIG. 11. When it is determined to be "absent" in the determination (NO), it is determined that the obtained sequence information is derived from a short amplicon (Step S216). Alternatively, instead of determining that the obtained sequence information is derived from a short amplicon in Step S216, it may be determined that the obtained sequence information is not used in Step S22 shown in FIG. 11. Although not shown, after Step S213, a processing unit 1010 may further discriminate whether the obtained sequence information is derived from an error-free amplicon or is derived from a long amplicon. This discrimination can be made by comparing the standard position of the search sequence with the nucleotide number at which position of the obtained sequence information the search sequence is located.

The processing unit 101 may perform processing to be described later shown in FIG. 20 after Step S23.

Figure 14:
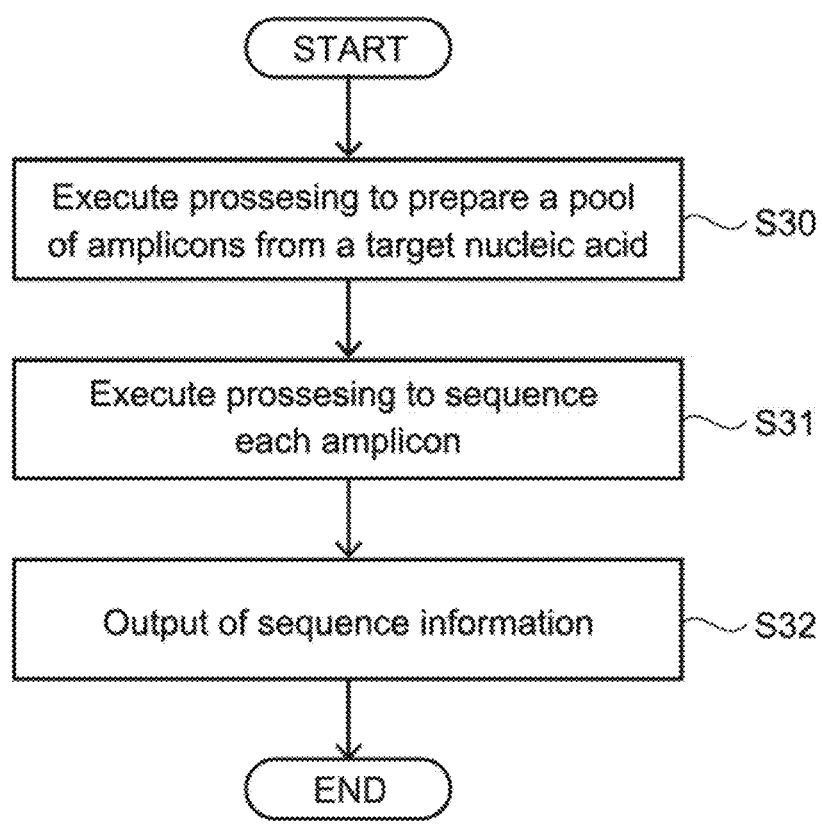
FIG. 14 is a flowchart showing an example of processing by the sequencing apparatus.

The processing unit 101 may make the amplicon preparing unit 31 execute processing to prepare amplicons from a target nucleic acid (Step S30) shown in FIG. 14, before Step S20 shown in FIG. 11. The processing unit 101 may make the sequencing unit 32 execute a processing for sequencing each amplicon amplified in Step S30 (Step S31). In this case, the target nucleic acid is set in the sequencing apparatus 30 by the user. In accordance with an instruction to start processing inputted from the input unit 111 by the user, the processing unit starts Step S30. Step S31 may be started in accordance with a user's instruction to start processing or may be continued after the end of Step S30.

Next, the processing unit 101 outputs the sequence information obtained by sequencing to the target nucleic acid sequencing apparatus 10 (Step S32).

For the same terms as the terms used in the above 1-3., the description is incorporated into the description of this section. [2-2. Second Target Nucleic Acid Sequencing Apparatus] [2-2-1. Hardware Configuration]

Figure 15A:
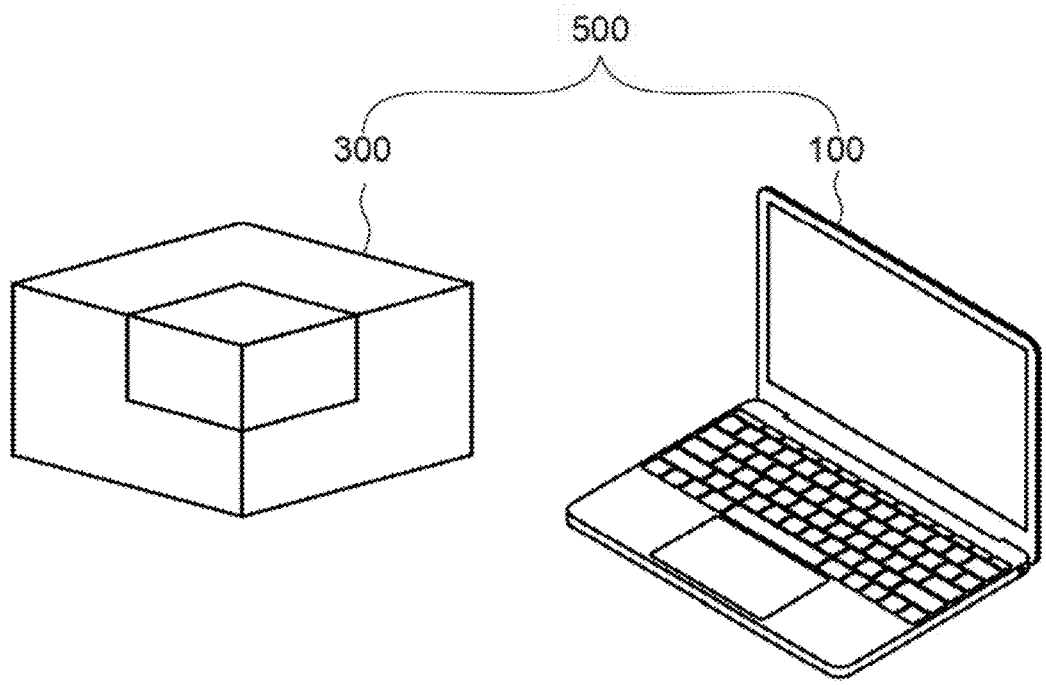
FIGS. 15A and 15B are diagrams showing a configuration of a second target nucleic acid sequencing apparatus.
Figure 15B:
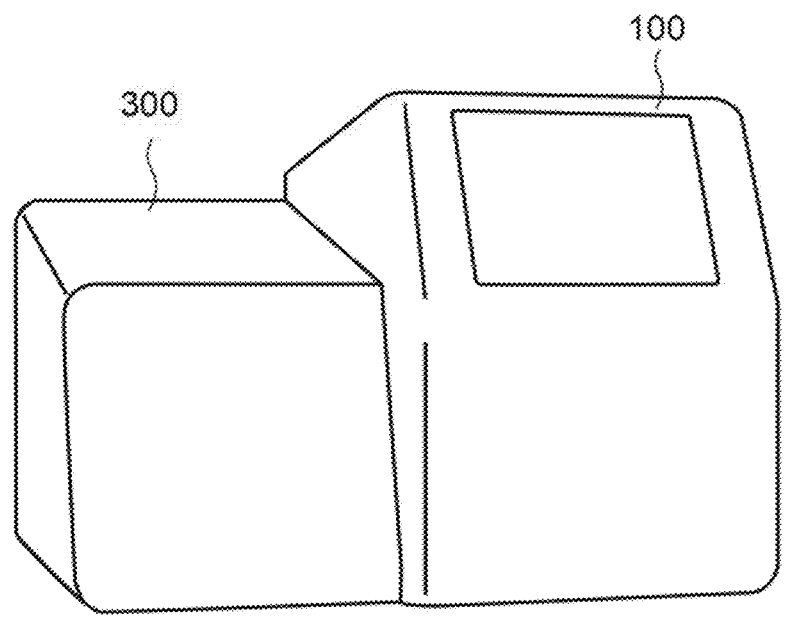
Figure 16:
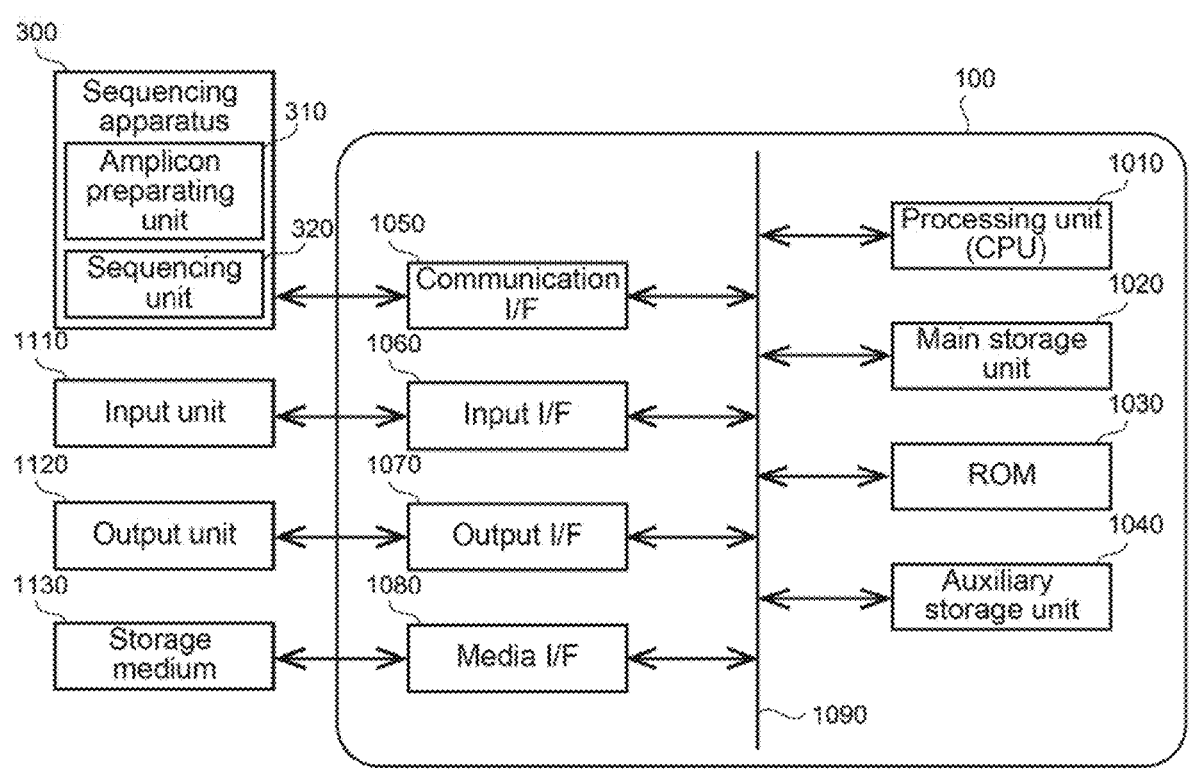
FIG. 16 is a diagram showing an outline of a hardware configuration of a second target nucleic acid sequencing apparatus.

FIG. 15 and FIG. 16 show the configuration of the target nucleic acid sequencing apparatus 100. The target nucleic acid sequencing apparatus 100 may be connected to an input unit 1110, an output unit 1120, and a storage medium 1130. The target nucleic acid sequencing apparatus 100 may be connected to a sequencing apparatus 300 that performs sequencing. The target nucleic acid sequencing apparatus 100 may constitute a target nucleic acid sequence sequencing system 500 connected to the sequencing apparatus 300 directly or via a network or the like (FIG. 15A). The target nucleic acid sequencing apparatus 100 and the sequencing apparatus 300 may be integrated as shown in FIG. 15B.

In FIG. 16, since the processing unit 1010, a main storage unit 1020, an ROM 1030, an auxiliary storage unit 1040, a communication interface 1050, an input interface 1060, an output interface 1070, a media interface 1080, a bus 1090, the input unit 1110, the output unit 1120, the storage medium 1130, the sequencing apparatus 300, an amplicon preparing unit 310, and a sequencing unit 320 correspond to the processing unit 101, the main storage unit 102, the ROM 103, the auxiliary storage unit 104, the communication interface 105, the input interface 106, the output interface 107, the media interface 108, the bus 109, the input unit 111, the output unit 112, the storage medium 113, the sequencing apparatus 30, the amplicon preparing unit 31 and the sequencing section 32 shown in FIG. 11, respectively, the description of the above 2-1-2 is incorporated in this section. [2-2-2. Operation of Second Target Nucleic Acid Sequencing Apparatus]

The operation of the target nucleic acid sequencing apparatus 100 will be described with reference to FIG. 17. The following operations are processed by the processing unit 1010 according to a computer program to be described later.

The processing unit 1010 obtains sequence information obtained by the sequencing apparatus 300, for example, in accordance with an instruction to start processing inputted from the input unit 1110 by the user (Step S40). At this time, for example, when reading sequence information by input from the input unit 1110 by the user, or from the sequencing apparatus 300, the processing unit 1010 obtains an identification number (subject ID) for identifying a subject from whom a sample was obtained, a sample identification ID for identifying the type (blood, tissue, formalin fixed/paraffin embedded (FFPE) tissue) of sample, an identification number (target nucleic acid identification ID) for identifying a target nucleic acid, an identification number (target region identification ID) for identifying a target nucleic acid, and the like. The obtained sequence information, identification ID and the like are stored in the main storage unit 1020 and/or the auxiliary storage unit 1040.

In accordance with the method described in the above 1-2., the processing unit 101 discriminates whether or not each sequence information obtained in Step S40 can be used for determining the accurate sequence of the target sequence, by the primer search described in the above 1-3. (Step S41). A specific flow of Step S41 is as described in FIG. 12 and the above 2-1-3.

In Step S41, the processing unit 101 determines the sequence discriminated to be usable for determining the accurate sequence of the target sequence, that is, the accurate sequence of the target region, based on the sequence information other than sequence information of short amplicon (sequence information of error-free amplicon and sequence information of long amplicon) (Step S42). A method for determining the accurate sequence of the target region will be described later with reference to FIG. 19.

Step S43 of determining whether or not there is a mutation in the accurate sequence of the target region determined in Step S42 may be performed. Details of Step 43 will be described later with reference to FIG. 20.

Figure 17:
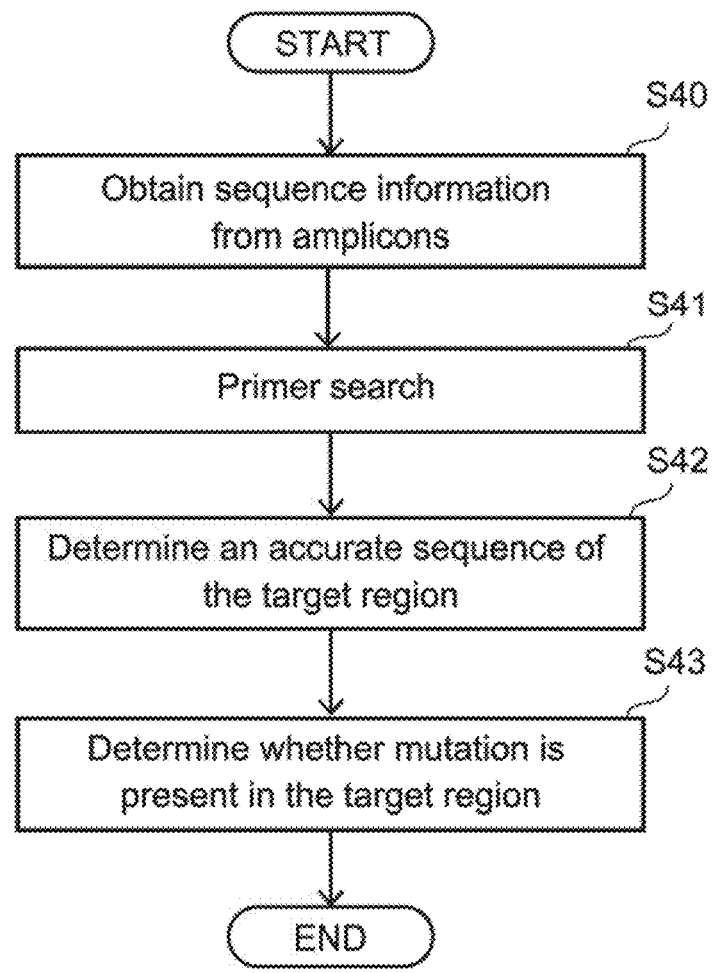
FIG. 17 is a flowchart showing an example of selection processing of sequence information used in the second target nucleic acid sequencing apparatus.
Figure 18:
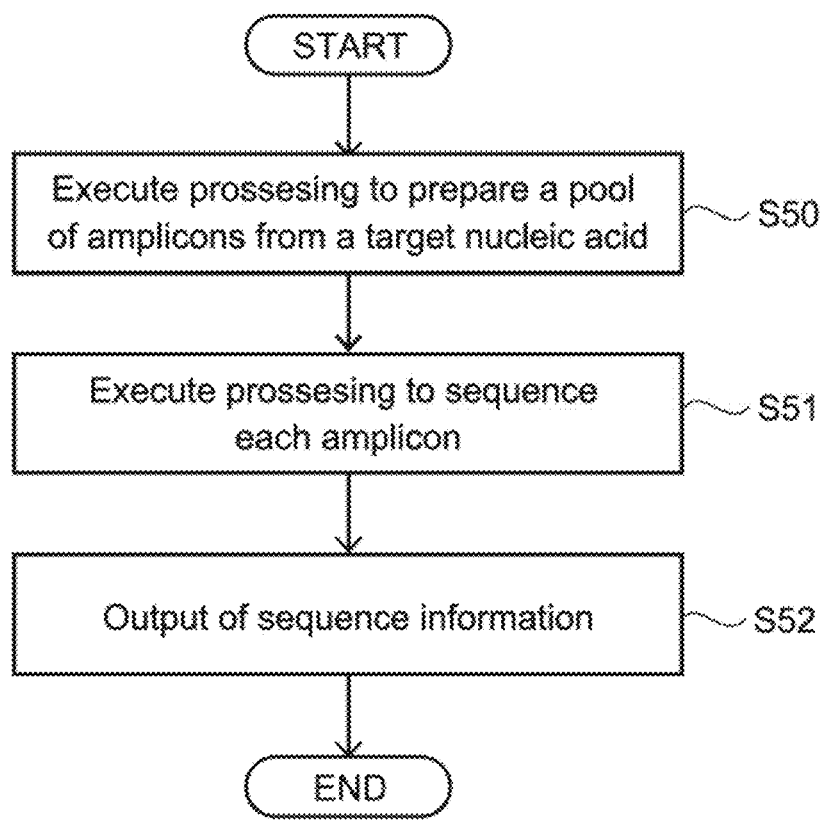
FIG. 18 is a flowchart showing an example of processing by the sequencing apparatus.

The processing unit 1010 may make the amplicon preparing unit 310 execute processing to prepare amplicons from a target nucleic acid (Step S50) shown in FIG. 18, before Step S40 shown in FIG. 17. The processing unit 1010 may make the sequencing unit 320 execute a processing for sequencing each amplicon amplified in Step S50 (Step S51). In this case, the target nucleic acid is set in the sequencing apparatus 300 by the user. In accordance with an instruction to start processing inputted from the input unit 1110 by the user, the processing unit starts Step S50. Step S51 may be started in accordance with a user's instruction to start processing or may be continued after the end of Step S50.

Next, the processing unit 1010 outputs the sequence information obtained by sequencing to the target nucleic acid sequencing apparatus 100 (Step S52).

For the same terms as the terms used in the above 1-3., the description is incorporated into the description of this section.

[2-3. Other Processing]

Figure 19:
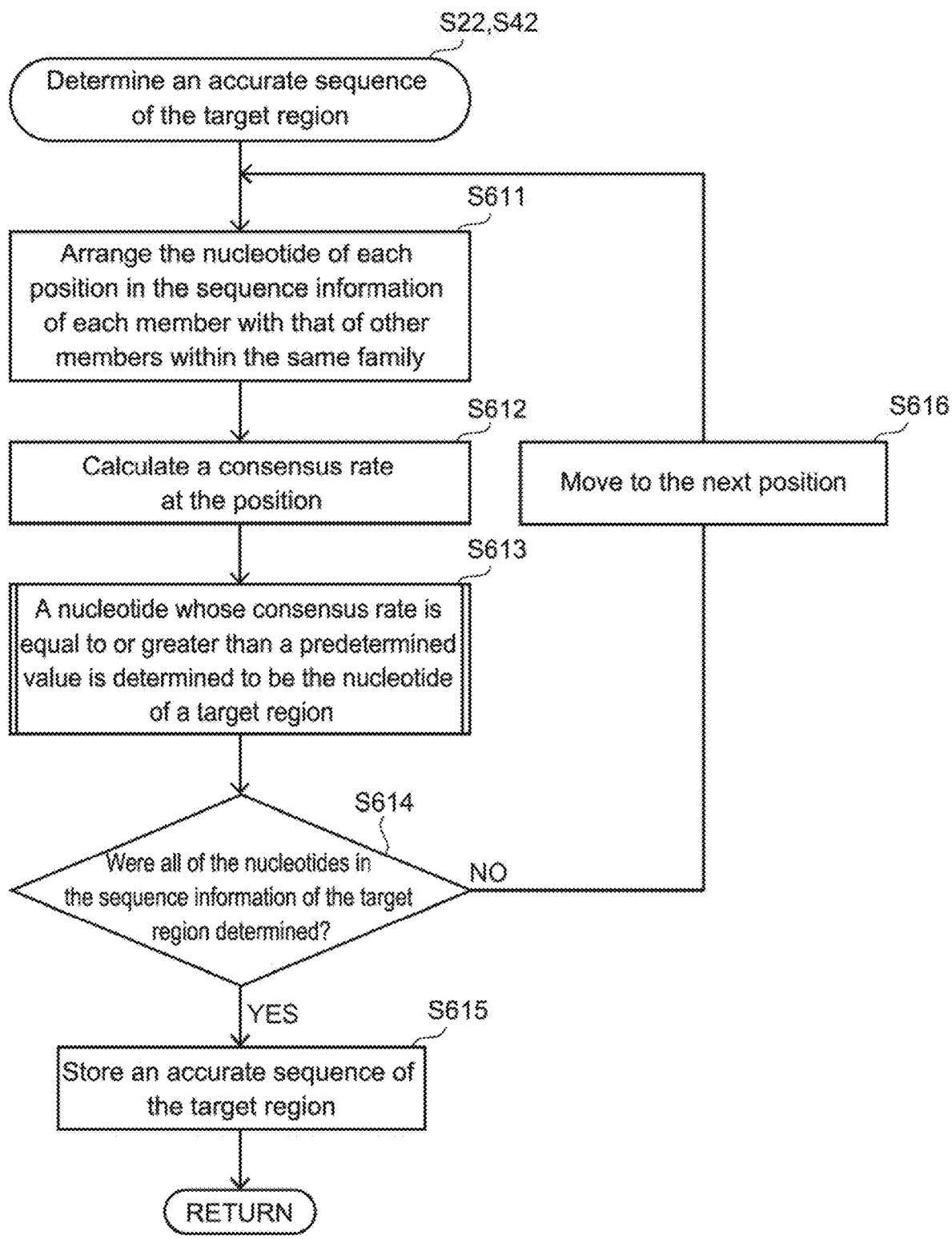
FIG. 19 is a flowchart showing a method for determining the sequence of a target region.

Further, the processing units 101 and 1010 may perform the processing for determining the target sequence shown in FIG. 19 in Step S22 of FIG. 11 or Step S42 of FIG. 17.

Next, an example of a processing for determining the accurate sequence of the target region will be specifically described, with reference to FIG. 19. The processing units 101 and 1010 perform the processing for determining the accurate sequence of the target region in Step S22 of FIG. 11 or S42 of FIG. 17. In this processing, the processing units 101 and 1010 first align a nucleotide of each position in the sequence information of each member with the same position of other members for each member within the family having the same UID sequence (Step S611).

Next, the processing units 101 and 1010 calculate the consensus rate of the position (Step S612).

The processing units 101 and 1010 compare the consensus rate calculated in Step S612 with the predetermined value of the consensus rate stored in the auxiliary storage units 104 and 1040, and the processing units 101 and 1010 determine a nucleotide whose consensus rate is equal to or larger than the predetermined value as the nucleotide of the target region (Step S613).

The processing units 101 and 1010 determine whether nucleotides have been determined for all positions in the target region. When nucleotides have not been determined for all positions in the target region, the processing units 101 and 1010 return to Step S611 and repeat Steps S611 to S614 until nucleotides are determined for all positions in the target region.

When nucleotides have been determined for all positions in the target region, the processing units 101 and 1010 proceed to Step S615, and an accurate sequence of the target region is stored in the auxiliary storage unit 104 or 1040, or the like.

The processing units 101 and 1010 may output the accurate sequence of the target region to the output units 112 and 1120.

Figure 20:
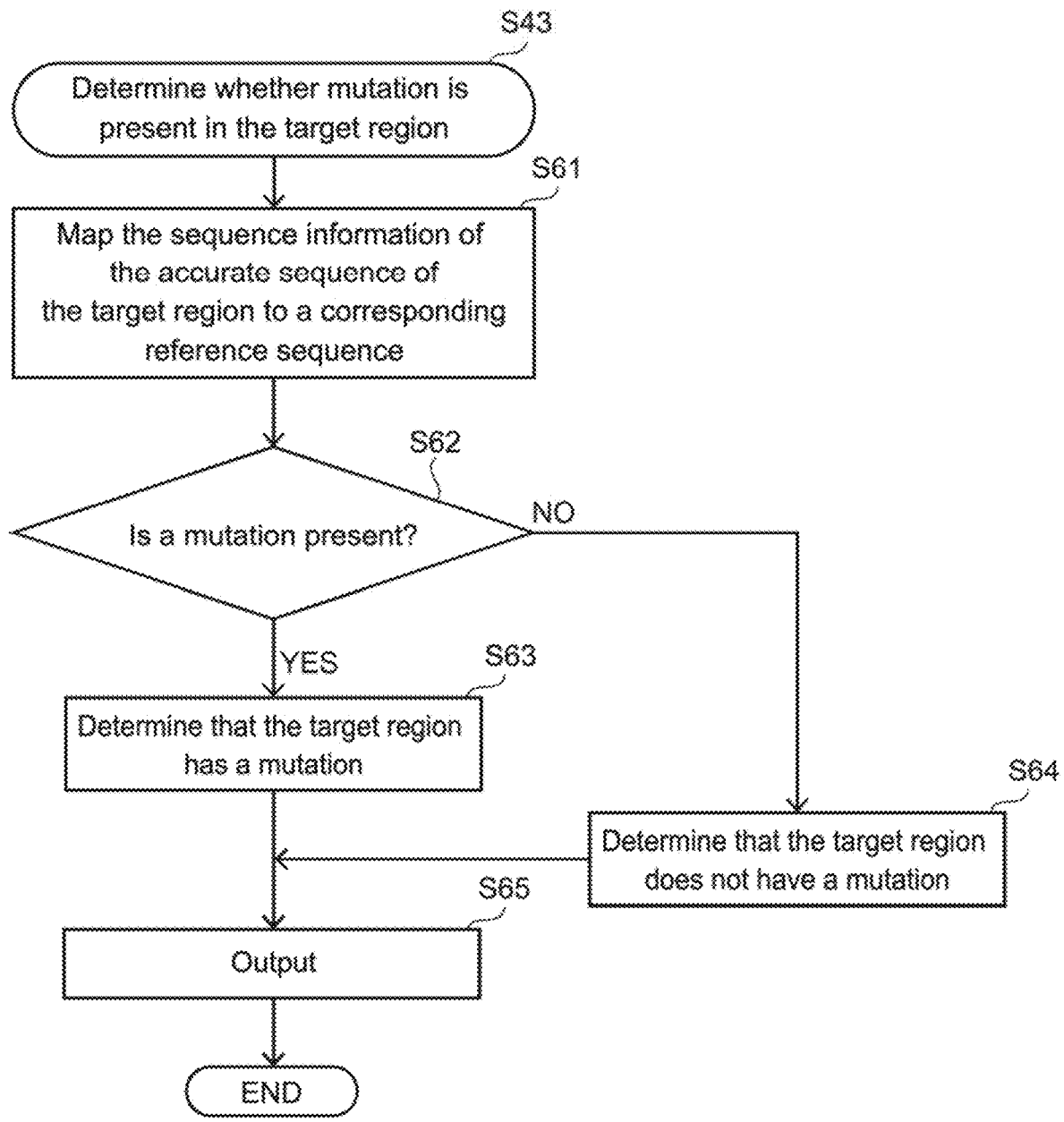
FIG. 20 is a flowchart showing accurate processing.

An example of a processing for determining whether or not there is a mutation in the sequence of the target region will be specifically described, with reference to FIG. 20. The processing units 101 and 1010 map the sequence information of the accurate sequence of the target region determined in Step S22 of FIG. 11 or S42 of FIG. 17 to a reference sequence corresponding to the sequence information (Step S61). The reference sequence is as described in the above 1-4. The reference sequence may be stored in the auxiliary storage units 104 and 1040, or may be obtained at the time of determining the sequence via a network. Mapping may be performed by sending the sequence information to a server or the like in which the reference sequence is stored via the network.

The processing units 101 and 1010 compare the sequence information with the reference sequence (including a mutated sequence registered in the mutation information database) by mapping.

The processing units 101 and 1010 determine whether or not there is a mutated sequence in the sequence information (Step S62).

When there is no mutated sequence in the sequence information, the processing units 101 and 1010 determine that the target region has no mutation (Step S63). When the mutated sequence is not an accurate mutation (NO), it is determined that there is no mutation in the target region (Step S64).

The processing units 101 and 1010 may store the determination results of the sequence of the target region in the auxiliary storage units 104 and 1040 or may output them to the output units 112 and 1120 (Step S65). As described in the above 1-4., the output destination can be a monitor of a sequencing apparatus, another terminal, a printer, or the like.

3. Computer Program

The computer program is a program for controlling the first target nucleic acid sequencing apparatus 10 and the first target nucleic acid sequence determining system 50, or the second target nucleic acid sequencing apparatus 100 and the second target nucleic acid sequence determination system 500, in the method for sequencing a target nucleic acid as described in the above 1.

The computer program controls the first target nucleic acid sequencing apparatus 10 and the first target nucleic acid sequence determining system 50 by making the processing unit 101 execute Steps S20 to S22 and Steps S211 to S214; Steps S30, S31, Steps S20 to S22, and Steps S211 to S214; Steps S20 to S22, Steps S211 to S214, and Steps S60 to S65; Steps S30, S31, Steps S20 to S22, Steps S211 to S214, and Steps S60 to S65, described in the above 2-1-2. and 2-3. The computer program controls the second target nucleic acid sequencing apparatus 100 and the second target nucleic acid sequence determination system 500 by making the processing unit 1010 execute Steps S40 to S44; Steps S50, S51, and Steps S40 to S44; Steps S40 to S44, Steps S61 to S65, and Steps S611 to S615; Steps S50, S51, Steps S40 to S44, Steps S61 to S65, and Steps S611 to S615, described in the above 2-2-2. and 2-3.

The computer program may be stored in a storage medium. That is, the computer program is stored in a semiconductor memory element such as a hard disk or a flash memory, or a storage medium such as an optical disk. The computer program may be stored in a storage medium connectable via a network such as a cloud server. The computer program may be in a download form or a program product stored in the storage medium.

The storage format of the program in the storage medium is not limited as long as the presented apparatus can read the program. Storage into the storage medium is preferably nonvolatile.

4. Analysis Example

Sequence analysis of KIT gene was performed using next generation sequencer MiSeq (registered trademark) of Illumina Inc. Three types of primer sets (KIT61, KIT54, and KIT47) were used. These primer sets amplify each different target region. All primer sets contain a universal primer section, an index section and a target-specific primer section as forward primers, and a target-specific primer section and a universal primer section as reverse primers. All indices were random sequences. The results are shown in Table 1.

As a result of the analysis, many amplicons containing a tag section sequence of 14 nucleotides or more (represented as ">14 nt" in Table 1) were detected. Although these amplicons can accurately read the sequence information of the target region, the tag section sequence contained an error and was thus excluded from the analysis. It was shown that, by also using these sequence information for sequence analysis of the target region, the depth of coverage of sequencing was improved and accuracy of sequencing could be improved.

TABLE 1

| Primer set | >14 nt (reads) | <14 nt (reads) |
|---|---|---|
| KIT61 | 3043 | 24953 |
| KIT54 | 2506 | 17752 |
| KIT47 | 1400 | 8658 |

">14 nt" refers to sequence information in which the UID was longer than 14 nt
"<14 nt" refers to sequence information in which the UID was shorter than 14 nt

The invention claimed is:

1. A method for determining a nucleotide sequence of a target nucleic acid, comprising:

providing a pool of amplicons, wherein the pool of amplicons comprises error-free amplicons and one or more error-containing long amplicons, and wherein said pool of amplicons is prepared by attaching a tag section to a target region in the target nucleic acid by conducting PCR using tagged oligonucleotide primer molecules to prepare tagged nucleic acid molecules, and amplifying the tagged nucleic acid molecules by PCR using a universal primer which hybridizes to a universal primer section in the tagged nucleic acid molecules to produce a pool of amplicons, wherein the tagged oligonucleotide primer molecules comprise the tag section at the 5' side thereof and a target-specific primer section at the 3' side of the tag section, wherein the tag section comprises the universal primer section at the 5' side thereof and an index section at the 3' side thereof, and wherein the error-free amplicons are produced from tagged oligonucleotide primer molecules in which the length of the index section is X nucleotides, and wherein the long amplicons comprise amplicons produced from tagged oligonucleotide primer molecules in which the length of the index section is greater than or equal to X+1 nucleotides, but less than or equal to X+40 nucleotides, wherein X is an integer from 4-30;

sequencing each amplicon in the pool of amplicons to obtain sequence information of each amplicon;

comparing a part of the sequence information of each amplicon with at least a part of the sequence of the target specific primer section, wherein the part of the sequence information of each amplicon is a sequence starting from position X+1;

determining whether the part of the sequence information of each amplicon comprises at least the part of the sequence of the target specific primer section; and determining sequence of the target region using sequence information which comprises at least the part of the sequence of the target-specific primer section, wherein said sequence information is obtained from error-free amplicons, and from one or more long amplicons, in said amplicon pool.

2. The method according to claim 1, wherein said pool of amplicons further comprises one or more error-containing short amplicons, and wherein the short amplicons comprise amplicons produced from tagged oligonucleotide primer molecules in which the length of the index section is greater than or equal to X−25 nucleotides, but less than or equal to X−1 nucleotides, wherein X is an integer from 4-30.

3. The method according to claim 1, wherein the number of nucleotides of the target-specific primer section is 10 to 50.

4. The method according to claim 1, wherein the index section comprises a random sequence.

5. The method according to claim 1, wherein the index section comprises a pre-defined sequence.

6. The method according to claim 1, wherein the index section is a unique identifier section.

7. The method according to claim 1, wherein the tag section further comprises an adaptor section at the 5' side of the universal primer section.

8. The method according to claim 1, wherein in the step of determining sequence, a sequence information that does not comprise at least the part of the sequence of the target-specific primer section is not used for determining sequence.

9. A method for determining a nucleotide sequence of a target nucleic acid, comprising:

determining a sequence of a target region by using sequence information obtained from each amplicon in a pool of amplicons, wherein, the amplicons in said pool of amplicons are prepared from template nucleic acids, wherein said pool of amplicons is prepared by attaching a tag section to a target region in the template nucleic acids by conducting PCR using tagged oligonucleotide primer molecules;

wherein the tagged oligonucleotide primer molecules comprise the tag section at the 5' side thereof and a target-specific primer section at the 3' side of the tag section, and wherein the tag section comprises an index section;

wherein the pool of amplicons comprises error-free amplicons and one or more error-containing long amplicons, wherein the error-free amplicons are produced from tagged oligonucleotide primer molecules in which the length of the index section is X nucleotides, and wherein the long amplicons comprise amplicons produced from tagged oligonucleotide primer molecules in which the length of the index section is greater than or equal to X+1 nucleotides, but less than or equal to X+40 nucleotides, wherein X is an integer from 4-30; and the sequence of the target region is determined by using sequence information obtained from error-free amplicons, and from one or more long amplicons, in said amplicon pool.

10. The method according to claim 9, further comprising obtaining the sequence information obtained from each of the amplicons before the determining step.

11. The method according to claim 10, further comprising preparing the pool of amplicons before the obtaining step.

12. The method according to claim 9, wherein said pool of amplicons further comprises one or more error-containing short amplicons, and wherein the short amplicons comprise amplicons produced from tagged oligonucleotide primer molecules in which the length of the index section is greater than or equal to X−25 nucleotides, but less than or equal to X−1 nucleotides, wherein X is an integer from 4-30.

13. The method according to claim 9, wherein the index section comprises a random sequence.

14. The method according to claim 9, wherein the index section is a unique identifier section.

15. The method according to claim 12, wherein the sequence of the target region is determined without using sequence information obtained from short amplicons in said amplicon pool.

* * * * *

SEQUENCE LISTING

<160> NUMBER OF SEQ ID NOS: 7

<210> SEQ ID NO 1
<211> LENGTH: 56
<212> TYPE: DNA
<213> ORGANISM: Artificial Sequence
<220> FEATURE:
<223> OTHER INFORMATION: Synthetic example sequence
<220> FEATURE:
<221> NAME/KEY: misc_feature
<222> LOCATION: (16)..(29)
<223> OTHER INFORMATION: n is a, c, g, or t

<400> SEQUENCE: 1
tcagtgctgc aacatnnnnn nnnnnnnnng gacaaggagg acctcttctc gatact        56

<210> SEQ ID NO 2
<211> LENGTH: 54
<212> TYPE: DNA
<213> ORGANISM: Artificial Sequence
<220> FEATURE:
<223> OTHER INFORMATION: Synthetic example sequence
<220> FEATURE:
<221> NAME/KEY: misc_feature
<222> LOCATION: (16)..(27)
<223> OTHER INFORMATION: n is a, c, g, or t

<400> SEQUENCE: 2
tcagtgctgc aacatnnnnn nnnnnngga caaggaggac ctcttctcga tact            54

<210> SEQ ID NO 3
<211> LENGTH: 58
<212> TYPE: DNA
<213> ORGANISM: Artificial Sequence
<220> FEATURE:
<223> OTHER INFORMATION: Synthetic example sequence
<220> FEATURE:
<221> NAME/KEY: misc_feature
<222> LOCATION: (16)..(31)
<223> OTHER INFORMATION: n is a, c, g, or t

<400> SEQUENCE: 3
tcagtgctgc aacatnnnnn nnnnnnnnnn nggacaagga ggacctcttc tcgatact      58

<210> SEQ ID NO 4
<211> LENGTH: 42
<212> TYPE: DNA
<213> ORGANISM: Artificial Sequence
<220> FEATURE:
<223> OTHER INFORMATION: Synthetic example sequence
<220> FEATURE:
<221> NAME/KEY: misc_feature
<222> LOCATION: (1)..(14)
<223> OTHER INFORMATION: n is a, c, g, or t

<400> SEQUENCE: 4
nnnnnnnnnn nnnncctgtt cctccctgga gaagagctat ga                        42

<210> SEQ ID NO 5
<211> LENGTH: 40
<212> TYPE: DNA
<213> ORGANISM: Artificial Sequence
<220> FEATURE:
<223> OTHER INFORMATION: Synthetic example sequence
<220> FEATURE:
<221> NAME/KEY: misc_feature
<222> LOCATION: (1)..(12)
<223> OTHER INFORMATION: n is a, c, g, or t

<400> SEQUENCE: 5

```
nnnnnnnnnn nncctgttcc tccctggaga agagctatga                    40

<210> SEQ ID NO 6
<211> LENGTH: 44
<212> TYPE: DNA
<213> ORGANISM: Artificial Sequence
<220> FEATURE:
<223> OTHER INFORMATION: Synthetic example sequence
<220> FEATURE:
<221> NAME/KEY: misc_feature
<222> LOCATION: (1)..(16)
<223> OTHER INFORMATION: n is a, c, g, or t

<400> SEQUENCE: 6
nnnnnnnnnn nnnnnncctg ttcctccctg gagaagagct atga               44

<210> SEQ ID NO 7
<211> LENGTH: 15
<212> TYPE: DNA
<213> ORGANISM: Artificial Sequence
<220> FEATURE:
<223> OTHER INFORMATION: Synthetic example sequence

<400> SEQUENCE: 7
cctgttcctc cctgg                                               15
```